(12) United States Patent
Grill et al.

(10) Patent No.: US 11,617,886 B2
(45) Date of Patent: Apr. 4, 2023

(54) STATE-DEPENDENT PERIPHERAL NEUROMODULATION TO TREAT BLADDER DYSFUNCTION

(71) Applicant: Duke University, Durham, NC (US)

(72) Inventors: Warren M. Grill, Chapel Hill, NC (US); James A. Hokanson, Morrisville, NC (US); Christopher L. Langdale, Apex, NC (US)

(73) Assignee: Duke University, Durham, NC (US)

( * ) Notice: Subject to any disclaimer, the term of this patent is extended or adjusted under 35 U.S.C. 154(b) by 0 days.

(21) Appl. No.: 16/897,392

(22) Filed: Jun. 10, 2020

(65) Prior Publication Data

US 2021/0038888 A1 Feb. 11, 2021

Related U.S. Application Data

(63) Continuation of application No. 15/767,400, filed as application No. PCT/US2016/057043 on Oct. 14, 2016, now Pat. No. 10,722,708.

(60) Provisional application No. 62/241,825, filed on Oct. 15, 2015.

(51) Int. Cl.
*A61N 1/36* (2006.01)
*A61N 1/05* (2006.01)
*A61N 1/372* (2006.01)
*A61K 45/06* (2006.01)

(52) U.S. Cl.
CPC ..... *A61N 1/36007* (2013.01); *A61N 1/36196* (2013.01); *A61K 45/06* (2013.01); *A61N 1/0556* (2013.01); *A61N 1/37235* (2013.01)

(58) Field of Classification Search
CPC ............ A61N 1/36007; A61N 1/36196; A61N 1/0556; A61N 1/37235
See application file for complete search history.

(56) References Cited

U.S. PATENT DOCUMENTS

| | | | |
|---|---|---|---|
| 10,722,708 B2 | 7/2020 | Grill et al. | |
| 2002/0193840 A1 | 12/2002 | Sawan et al. | |
| 2009/0036945 A1 | 2/2009 | Chancellor et al. | |
| 2009/0326603 A1* | 12/2009 | Boggs, II | A61N 1/36196 607/41 |
| 2010/0076254 A1 | 3/2010 | Jimenez et al. | |
| 2011/0118805 A1 | 5/2011 | Wei et al. | |
| 2012/0197337 A1 | 8/2012 | Su et al. | |
| 2018/0296833 A1 | 10/2018 | Grill et al. | |

FOREIGN PATENT DOCUMENTS

| | | |
|---|---|---|
| CN | 202875787 U | 4/2013 |
| CN | 103269692 A | 8/2013 |
| EP | 1424079 A1 | 6/2004 |
| JP | 2006-509752 A | 3/2006 |
| JP | 2007-075304 A | 3/2007 |
| JP | 20180519373 | 2/2021 |
| WO | WO 2008/153726 A2 | 12/2008 |

* cited by examiner

*Primary Examiner* — Paula J Stice
(74) *Attorney, Agent, or Firm* — Wolf, Greenfield & Sacks, P.C.

(57) ABSTRACT

The present invention relates to a neuromodulation apparatus and methods of using the neuromodulation apparatus for treating bladder dysfunction.

18 Claims, 12 Drawing Sheets

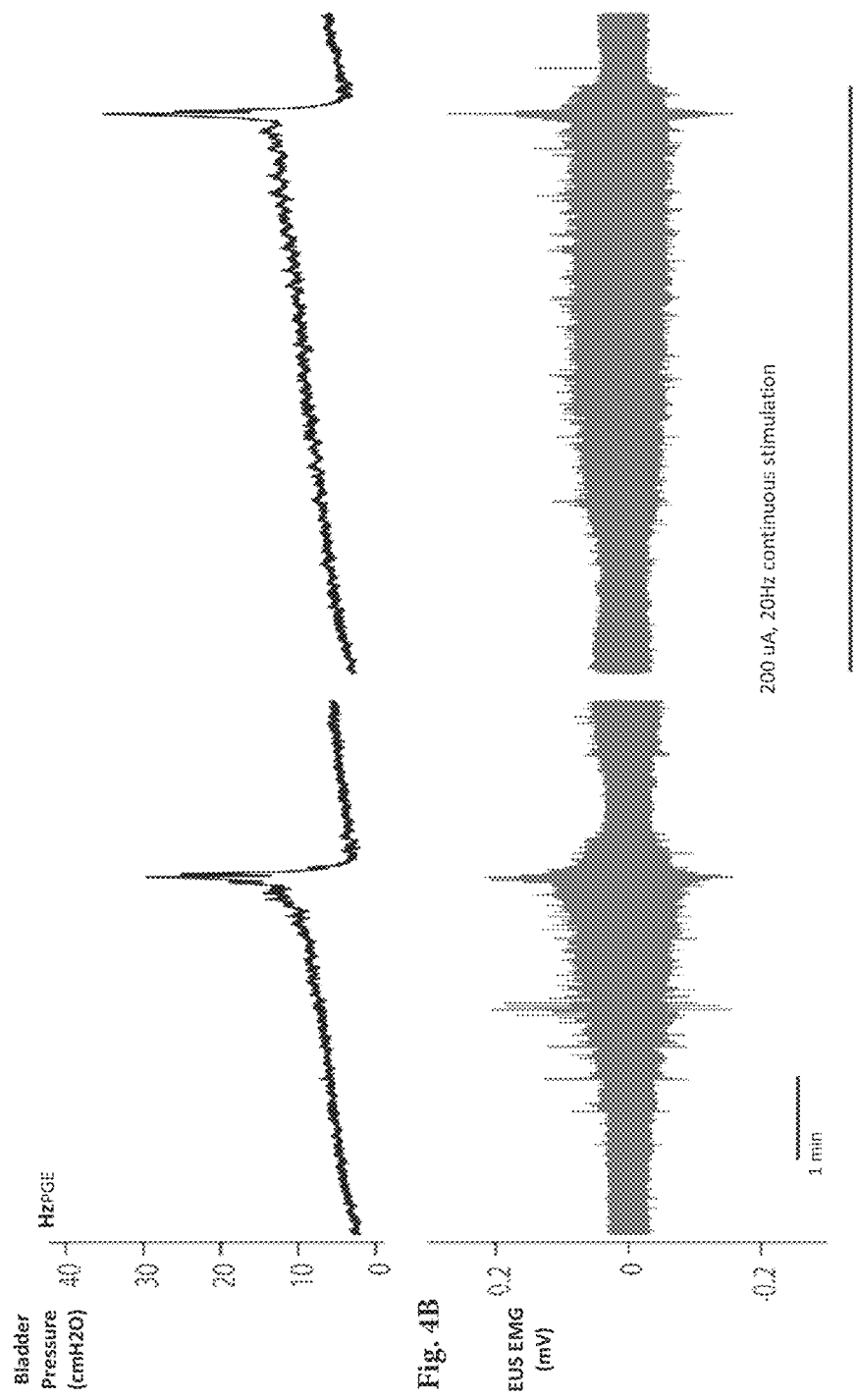

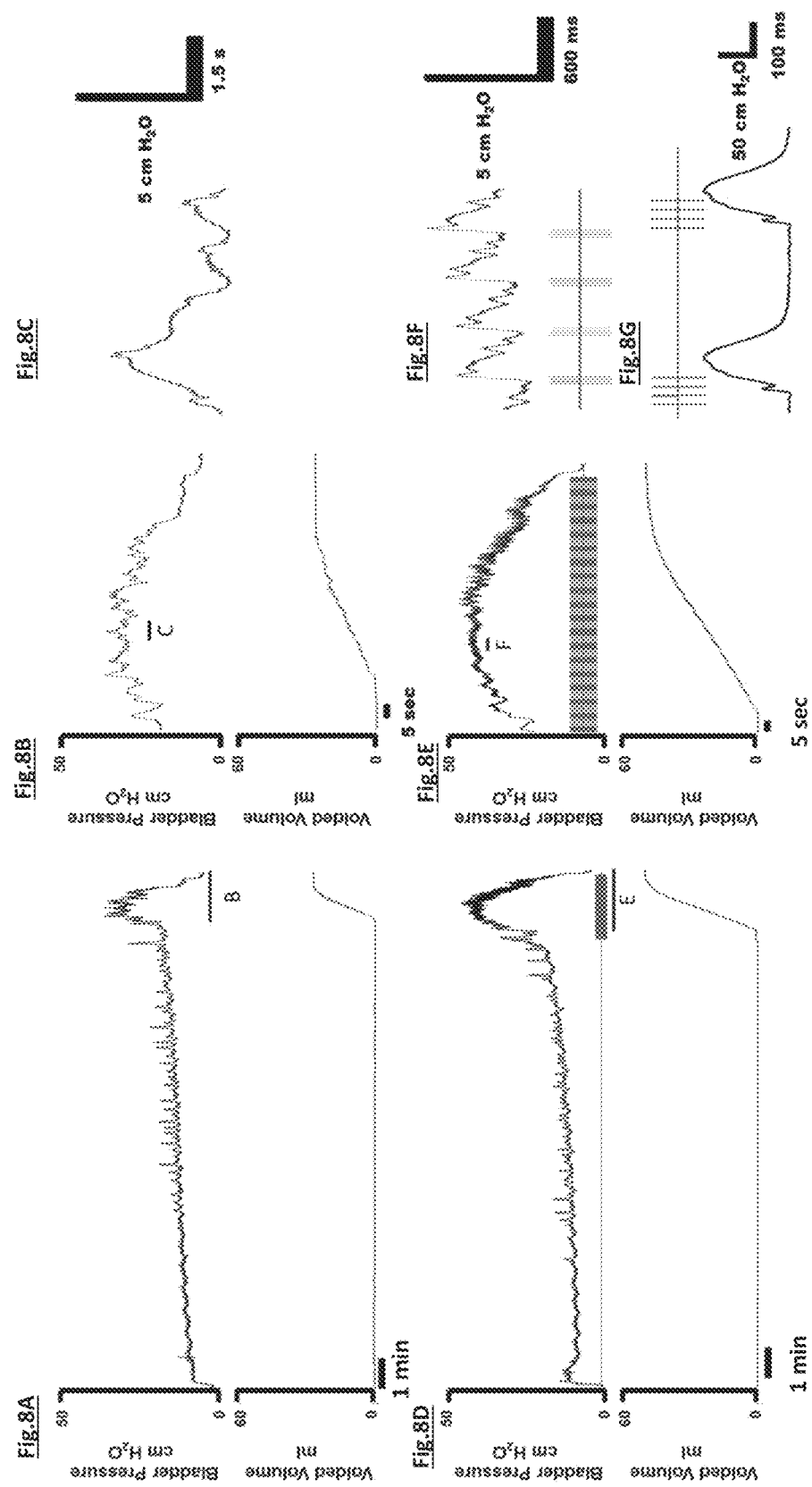

STATE-DEPENDENT PERIPHERAL NEUROMODULATION TO TREAT BLADDER DYSFUNCTION

RELATED APPLICATIONS

This application is a continuation of U.S. application Ser. No. 15/767,400, filed Apr. 11, 2018, now U.S. Pat. No. 10,722,708, which is a national stage filing under 35 U.S.C. 371 of international patent application number PCT/US2016/057043, filed Oct. 14, 2016, which claims the benefit under 35 U.S.C. § 119(e) of U.S. provisional application number 62/241,825, filed Oct. 15, 2015, the entire contents of each of which are incorporated herein by reference in their entireties.

BACKGROUND

Efficient bladder function, mediated by continence and micturition reflexes, is accomplished through coordinated sympathetic, parasympathetic and somatic neural activity [Beckel and Holstege Neurophysiology of the Lower Urinary Tract, in *Urinary Tract* (2011) Springer Berlin Heidelberg, 149-169].

Treatments for bladder dysfunction include behavioural therapy, exercise therapy, and pharmacotherapy. Behavioural and exercise therapy have limited efficacy, and pharmacotherapy has dose-limiting side effects. Overactive bladder (OAB), resulting in urgency, frequency and incontinence, is a highly prevalent condition that leads to medical complications and decreased quality of life [Latini & Giannantoni (2011), Expert Opinion on Pharmacotherapy 12:1017-1027].

In patients who are non-responsive or whose condition is inadequately controlled by conservative treatments, attempts have been made to control the functioning of the urinary bladder using electrical devices, as summarized by Gaunt and Prochazka (Progress in Brain Research 152:163-94 (2006)). The FDA-approved use of sacral neuromodulation (SNM) targeting the sacral spinal nerves (INTERSTIM™ therapy of Medtronic, Inc (Minneapolis, Minn.)) has proved partially successful. The Medtronic system uses a cylindrical electrode inserted in the S3 sacral foramen (a bony tunnel in the pelvis) adjacent to the S3 spinal nerve. Approximately half of screened subjects go on to receive an implant, and only around 75% of implant recipients experience a ≥50% reduction in leaking episodes (Schmidt, et al. Sacral nerve stimulation for treatment of refractory urinary urge incontinence, (1999) J Urol. 162(2):352-7). Further, in a multi-centre clinical trial of 98 implanted patients, surgical revision was required in 32.5% of recipients, illustrating the complexity of the spinal nerve approach (Van Voskuilen A C, et al. Medium-term experience of sacral neuromodulation by tined lead implantation. *BJU Int* 2007;99:107-10; Pham K, et al. Unilateral versus bilateral stage I neuromodulator lead placement for the treatment of refractory voiding dysfunction. *Neurourol Urodyn* 2008; 27:779-81).

Bladder function is comprised of two phases: a filling phase (urine storage) and a voiding phase (urine evacuation). Despite this biphasic process, current artificial electric stimulation protocols do not differentiate between the phases, even though the goals of these phases are diametrically opposed. Instead, it is customary to stimulate with a fixed stimulus amplitude, rate and pulse width throughout the day. Advanced features allow for intervening periods of stimulation and no stimulation (cycling), although this is principally to prolong battery life rather than to specifically target urine storage or voiding (Medtronic INTERSTIM™ Programming Guide), and is not timed with respect to periods of continence (filling or storage) or voiding (micturition or urination).

It would be desirable to provide improved apparatus and methods to provide for control of bladder function.

SUMMARY OF INVENTION

The pudendal nerve is a somatic nerve (i.e. not autonomic) that innervates the urethra, external urethral sphincter, external anal sphincter, and perineal skin and carries afferent and efferent signals (FIG. 1). Other peripheral nerves innervating the bladder and lower urinary tract include the hypogastric nerve, an autonomic (sympathetic) nerve that innervates the bladder and urethra and carries afferent and efferent signals (FIG. 1), and the pelvic nerve, an autonomic (parasympathetic) nerve that also innervates the bladder and urethra and carries afferent and efferent signals.

The present inventors have shown herein that stimulation of the pudendal nerve can lead to an increase in bladder capacity. Surprisingly, the inventors further identified that the high level of stimulation required to achieve said increase in bladder capacity leads to a decrease in bladder voiding efficiency. This means that the parameters effective at promoting urine storage and continence led to a reduction in the ability to void the bladder. Efficient action of both aspects is required for normal bladder function.

However, as shown herein, stimulation of the pudendal nerve can also increase voiding efficiency if the appropriate stimulation is applied. Based on this observation, the inventors identified that phase-specific pudendal nerve stimulation can provide effective treatment to all aspects of bladder dysfunction. That is, by tailoring the nature of the stimulation applied to the nerve to the ongoing or desired phase of the bladder activity cycle, it is possible to both improve the filling and storage function of the bladder, and also improve the voiding function of the bladder.

Thus, the apparatuses and methods provided herein address the problem of treating bladder dysfunction using electrical apparatuses by applying phase-specific stimulation to the pudendal nerve in order to achieve the appropriate effect. These apparatuses and methods have the advantage of providing greater control of bladder function, whilst not requiring significant and potentially dangerous spinal surgery in order to position apparatuses in signalling contact with these nerves. In addition, the apparatuses and methods are able to match more closely the subject's activities, with the phase-specific stimulation ensuring that the appropriate bladder function (filling and storage, or voiding) is augmented at any given time, rather than the stimulation acting in conflict to the subject (e.g. when the subject wishes to initiate bladder voiding but stimulation is causing storage and preventing voiding).

Therefore, in a first aspect, the invention provides an apparatus for stimulating neural activity in a pudendal nerve of a subject, the apparatus comprising: at least one transducer configured to apply a signal to said nerve; and a controller coupled to the transducer(s) and controlling the signal to be applied by the transducer(s), wherein the controller is configured to cause at least one transducer to apply a first signal that stimulates neural activity in the pudendal nerve to produce a first physiological response in the subject, and the controller is configured to cause at least one transducer to apply a second signal that stimulates neural activity in the pudendal nerve to produce a second physiological response in the subject, wherein the first physiological response and second physiological response are different.

In a second aspect, the invention provides a method of treating bladder dysfunction in a subject comprising: (i) implanting in the subject an apparatus according to the first aspect; (ii) positioning at least one transducer of the apparatus in signalling contact with a pudendal nerve of the subject; and (iii) activating the apparatus. In certain embodiments, the first signal and second signal are applied to effect phase-specific stimulation of neural activity in the pudendal nerve.

In a third aspect, the invention provides a method of treating bladder dysfunction in a subject by phase-specific stimulation of neural activity in a pudendal nerve of the subject, the method comprising: applying a first signal that stimulates neural activity in the pudendal nerve to produce a first physiological response in the subject, and applying a second signal that stimulates neural activity in the pudendal nerve to produce a second physiological response in the subject, wherein the first physiological response and second physiological response are different. In certain embodiments, the first signal is applied during a filling phase and the second signal is applied to trigger micturition and/or applied during a voiding phase.

In a fourth aspect, the invention provides a use of a neuromodulation apparatus for treating bladder dysfunction in a subject by phase-specific stimulation of neural activity in a pudendal nerve of the subject.

In a fifth aspect the invention provides a neuromodulation system, the system comprising a plurality of apparatuses according to the first aspect. In such a system, each apparatus may be arranged to communicate with at least one other apparatus, optionally all apparatuses in the system. In certain embodiments, the system is arranged such that, in use, the apparatuses are positioned to bilaterally stimulate the pudendal nerves of a patient.

In a sixth aspect, the invention provides a pharmaceutical composition comprising a compound for treating bladder dysfunction, for use in a method of treating bladder dysfunction in a subject, wherein the method is a method according to the second aspect of the invention or according to the third aspect of the invention, the method further comprising the step of administering an effective amount of the pharmaceutical composition to the subject. It is a preferred embodiment that the pharmaceutical composition is for use in a method of treating bladder dysfunction wherein the method comprises applying a signal to a part or all of a pudendal nerve of said patient to stimulate the neural activity of said nerve in the patient, the signal being applied by a neuromodulation apparatus.

In a seventh aspect, the invention provides a pharmaceutical composition comprising a compound for treating bladder dysfunction, for use in treating bladder dysfunction in a subject, the subject having an apparatus according to the first aspect implanted. That is, the pharmaceutical composition is for use in treating a subject that has had an apparatus as described according to the first aspect implanted. The skilled person will appreciate that the apparatus has been implanted in a manner suitable for the apparatus to operate as described. Use of such a pharmaceutical composition in a patient having an apparatus according to the first aspect implanted will be particularly effective as it permits a cumulative or synergistic effect as a result of the combination of the compound for treating bladder dysfunction and apparatus operating in combination.

In preferred embodiments of all aspects of the invention, the subject is a human.

BRIEF DESCRIPTION OF THE DRAWINGS

Figures

FIGS. 4A-4B: Bladder pressure (FIG. 4A) and external urethral sphincter (EUS) electromygraphic (EMG) activity (FIG. 4B) recorded in a urethane anesthetized rat following installation of PGE2 in the bladder and during the delivery of "high intensity" pudendal nerve stimulation.

FIG. 6A: No stimulation: the bladder capacity was 0.49 ml and voiding efficiency was 56%. "High intensity" pudendal nerve stimulation increased bladder capacity to 0.63 ml, but had only a marginal effect on voiding efficiency (=62%). FIG. 6B: Phase-specific stimulation: Switching stimulation intensity from "high" during the filling phase to "low" during the voiding phase increased both bladder capacity (=0.67 ml) and voiding efficiency (=82%).

FIG. 7A: Bladder pressure during a distention evoked trial resulting in a bladder capacity (BC) of 9.1 ml and voiding efficiency (% VE) of 29%. FIG. 7B: Bladder pressure during pudendal stimulation at 50 µA at 10 Hz resulting in a BC of 8.5 ml and a VE of 30%. FIG. 7C: Bladder pressure during pudendal stimulation at 60 µA at 10 Hz resulting in a BC of 8.5 ml and a VE of 13%. FIG. 7D: Bladder pressure during pudendal stimulation at 200 µA at 20 Hz resulting in a BC of 20 ml and a VE of 20%. Stimulation is turned on at the start of the cystometrogram and is subsequently turned off after the end of the void. Each stimulation pulse was biphasic with a 100 us duration for each phase.

FIGS. 8A-8G: Example cystometrogram trials in cats during distention evoked voiding (FIGS. 8A-8C) and distention evoked voiding with unilateral phasic stimulation (FIGS. 8D-8F) of the pudendal somatic motor branch (DPeriN). FIG. 8A: Bladder pressure (top) and voided volume (bottom) during a distention evoked trial. FIG. 8B:

An expanded trace from FIG. 8A showing bladder pressure (top) and voided volume during the bladder contraction. FIG. 8C: An expanded view of the bladder pressure demonstrating the absence of high frequency oscillations (HFOs) during a void event. (FIG. 8D: Bladder pressure (top) and voided volume (bottom) during DPeriN phasic stimulation (red trace). DPeriN stimulation is turned on during a voiding event and is subsequently turned off after the end of the void. FIG. 8E: An expanded trace from FIG. 8D showing bladder pressure (top) and voided volume during the bladder contraction. DPeriN phasic stimulation (red trace) elicited HFOs during stimulation. FIG. 8F: An expanded view of the bladder pressure during phasic stimulation. Oscillations in bladder pressure follow each stimulation burst. FIG. 8G: Example of urethral pressure in response to 2 Hz bursts of DPeriN stimulation. Urethral pressure recorded during bladder empty conditions. The inter-pulse frequency was 40 Hz, and each burst was 100 ms in duration.

FIG. 9A: Bladder contraction amplitude evoked by artificial phasic stimulation was significantly larger than distention controls in both the intact and bilateral pudendal motor transection conditions. Phasic stimulation evoked increase in bladder contraction amplitude was abolished after complete bilateral pudendal transection (motor and sensory). FIG. 9B: Artificial phasic stimulation did not significantly decrease bladder contraction AUC compared to distention controls in intact, bilateral pudendal motor transection, and complete bilateral pudendal transection (motor and sensory) conditions. FIG. 9C: Artificial phasic stimulation significantly increased % voiding efficiency compared to distention controls in both the intact and bilateral pudendal motor transection conditions. Phasic stimulation evoked increase in % voiding efficiency was abolished after complete bilateral pudendal transection (motor and sensory).

Figure 1:
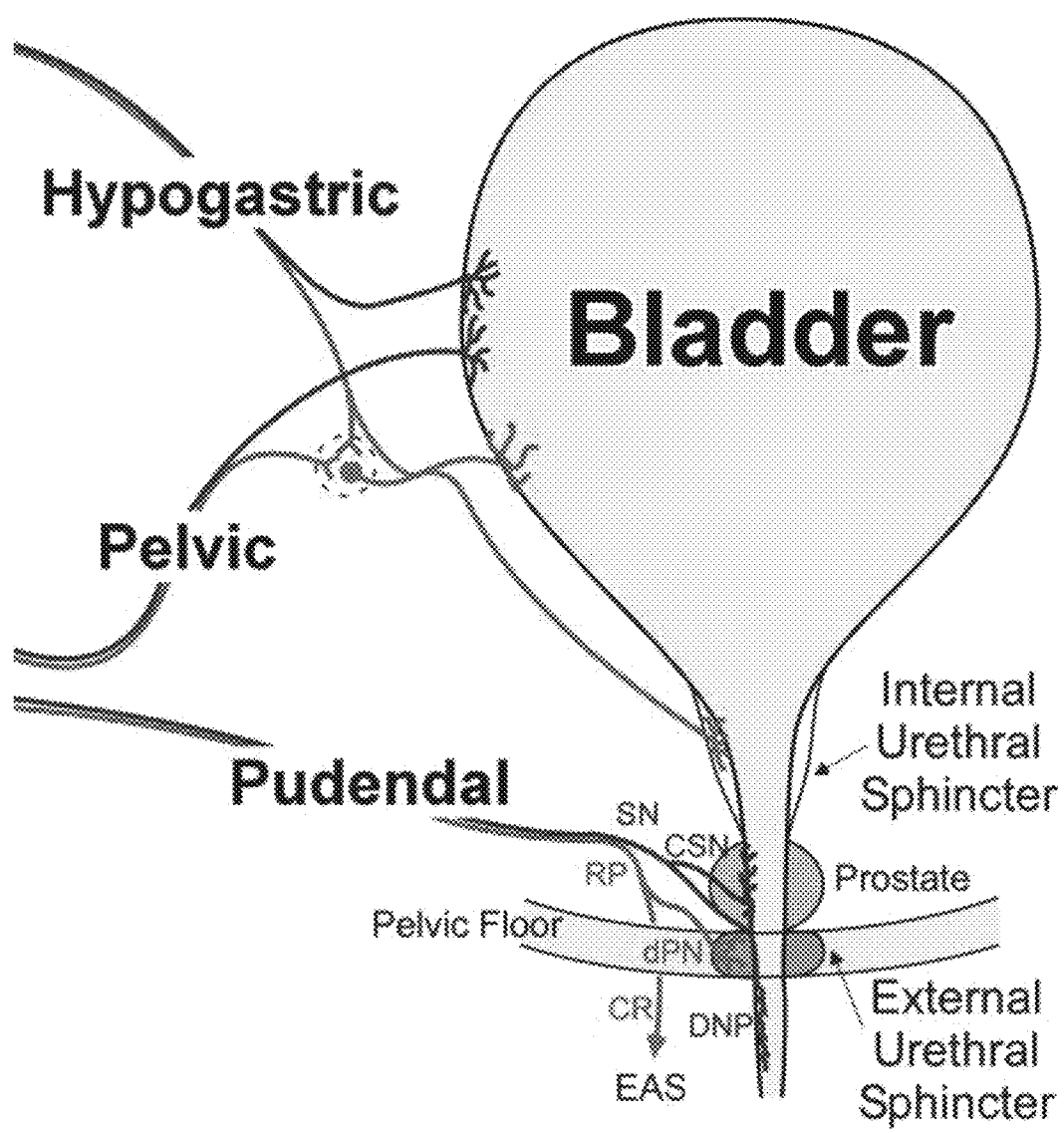
FIG. 1: Schematic drawing showing innervation of the bladder, internal urethral sphincter (IUS), external urethral sphincter (EUS) and prostate. Sensory branch of the pudendal nerve (SN), rectal perineal branch of the pudendal nerve (RP), cranial sensory branch of the pudendal nerve (CSN), dorsal nerve of the penis branch of the pudendal nerve (DNP; or clitoris), deep perineal branch of the pudendal nerve (dPN) and caudal rectal branch of the pudendal nerve (CR).

The terms as used herein are given their conventional definition in the art as understood by the skilled person, unless otherwise defined below. In the case of any inconsistency or doubt, the definition as provided herein should take precedence.

As used herein, "application of a signal" may equate to the transfer of energy in a suitable form to carry out the intended effect of the signal. That is, application of a signal to a nerve or nerves may equate to the transfer of energy to (or from) the nerve(s) to carry out the intended effect. For example, the energy transferred may be electrical, mechanical (including acoustic, such as ultrasound), electromagnetic (e.g. optical), magnetic or thermal energy. It is noted that application of a signal as used herein does not include a pharmaceutical intervention.

As used herein, "transducer" is taken to mean any element of applying a signal to the nerve or plexus, for example an electrode, diode, Peltier element or ultrasound actuator.

As used herein, "neural activity" of a nerve is taken to mean the signalling activity of the nerve, for example the amplitude, frequency and/or pattern of action potentials in the nerve.

"Modulation of neural activity", as used herein, is taken to mean that the signalling activity of the nerve is altered from the baseline neural activity—that is, the signalling activity of the nerve in the subject prior to any intervention. Such modulation may increase, inhibit, block, or otherwise change the neural activity compared to baseline activity.

"Stimulation of neural activity" as used herein may be an increase in the total signalling activity of the whole nerve, or that the total signalling activity of a subset of nerve fibres of the nerve is increased, compared to baseline neural activity in that part of the nerve. In a preferred embodiment, the modulation of neural activity is an increase in the signalling activity of the sensory fibres of the nerve, optionally a selective increase in the signalling activity of the sensory fibres of the nerve. A selective increase in neural activity of the sensory fibres causes a preferential increase in neural activity in the sensory fibres compared to any increase in neural signalling in the motor nerve fibres of the pudendal nerve. In a preferred alternative embodiment, the modulation of neural activity is an increase in the signalling activity of the motor fibres of the nerve, optionally a selective increase in the signalling activity of the motor fibres of the nerve. A selective increase in neural activity of the motor fibres causes a preferential increase in neural activity in the motor fibres compared to any increase in neural signalling in the sensory nerve fibres of the pudendal nerve.

"Modulation of neural activity" may also be an alteration in the pattern of action potentials. It will be appreciated that the pattern of action potentials can be modulated without necessarily changing the overall frequency. For example, modulation of the neural activity may be such that the pattern of action potentials is altered to more closely resemble a healthy state rather than a disease state—i.e. to more closely resemble the pattern in a healthy individual.

"Phase-specific" or "phase-specific stimulation" are each taken to mean that a different stimulation is applied depending on the ongoing and/or desired phase of the normal bladder activity cycle. The bladder activity cycle is characterised by a filling phase (also referred to as a storage phase), followed by a triggering of the micturition, followed by a voiding phase (also referred to as the micturition phase). A normal bladder activity cycle is a bladder activity cycle characteristic of a healthy individual.

The "ongoing phase" of bladder activity is the phase of the bladder activity cycle occurring at a particular given time. That a subject is in a given phase of the cycle can be indicated by a physiological parameter relevant to bladder activity, for example bladder pressure. For example, that a subject is in the filling phase may be indicated by increasing bladder pressure, or a sustained bladder pressure indicating that the bladder is at least partially filled. Triggering of micturition may be indicated by a sharp increase in bladder pressure. Other physiological parameters relevant to bladder activity include nerve activity in the pudendal nerve, nerve activity in the hypogastric nerve, nerve activity in the pelvic nerve, muscle activity in the bladder detrusor muscle, muscle activity in the internal urethral sphincter, muscle activity in the external urethral sphincter (EUS), muscle activity in the external anal sphincter.

The "desired phase" of the bladder activity cycle is the phase of the bladder activity cycle of which the subject is desirous. The desired phase may depend on the behaviour of the subject, for example whether they are sleeping, at exercise, at work, etc. Similarly, the desired phase may depend on perceived levels of urinary comfort. For example, the subject may perceive discomfort due to the sensation of having a full bladder, and therefore be desirous of triggering micturition.

It will be appreciated that phase-specific stimulation can take into account both ongoing and desirous phases of the bladder activity cycle. For example, a first stimulating signal may be applied (e.g. to increase bladder capacity) during a filling phase indicated by increasing bladder pressure, and a second stimulating signal may be applied when the subject is desirous of beginning micturition (e.g. to trigger micturition), or during a voiding phase as indicated by a change in muscle activity in the EUS (e.g. to increase voiding efficiency).

As used herein, a "healthy individual" or "healthy subject" is an individual not exhibiting any disruption or perturbation of normal bladder activity.

As used herein, "bladder dysfunction" is taken to mean that the patient or subject is exhibiting disruption of bladder function compared to a healthy individual. Bladder dysfunction may be characterised by symptoms such as nocturia, increased urinary retention, increased incontinence, increased urgency of urination or increased frequency of urination compared to a healthy individual. Bladder dysfunction includes conditions such as overactive bladder (OAB), neurogenic bladder, stress incontinence, and chronic urinary retention.

As used herein, an "improvement in a measurable physiological parameter" is taken to mean that for any given physiological parameter, an improvement is a change in the value of that parameter in the subject towards the normal value or normal range for that value—i.e. towards the expected value in a healthy individual.

For example, in a subject with bladder dysfunction, an improvement in a measurable parameter may be: a reduction in number of incontinence episodes, a decrease in urgency of urination, a decrease in frequency of urination, an increase in bladder capacity, an increase in bladder voiding efficiency, and/or a change in external urethral sphincter (EUS) activity towards that of a healthy individual, assuming the subject is exhibiting abnormal values for the respective parameter.

As used herein, a physiological parameter is not affected by modulation of the neural activity if the parameter does not change as a result of the modulation from the average value of that parameter exhibited by the subject or subject when no intervention has been performed—i.e. it does not depart from the baseline value for that parameter.

The skilled person will appreciate that the baseline for any neural activity or physiological parameter in an individual need not be a fixed or specific value, but rather can fluctuate within a normal range or may be an average value with associated error and confidence intervals. Suitable methods for determining baseline values would be well known to the skilled person.

As used herein, a measurable physiological parameter is detected in a subject when the value for that parameter exhibited by the subject at the time of detection is determined. A detector is any element able to make such a determination.

A "predefined threshold value" for a physiological parameter is the value for that parameter where that value or beyond must be exhibited by a subject or subject before the intervention is applied. For any given parameter, the threshold value may be defined as a value indicative of a pathological state (e.g. the subject is experiencing abnormal retention of urine) or a particular physiological state (e.g. the subject having a full bladder), or a particular behavioural state (e.g. the subject wishes to being voiding/micturition). Examples of such predefined threshold values include: bladder pressure abnormal compared to a healthy individual, bladder pressure indicative of bladder at or near capacity, abnormal peripheral nerve activity (for example, pudendal nerve, hypogastric nerve or pelvic nerve) compared to a healthy individual, abnormal EUS activity compared to a healthy individual (for instance an increase in EUS activity). Such a threshold value for a given physiological parameter is exceeded if the value exhibited by the subject is beyond the threshold value—that is, the exhibited value is a greater departure from the normal or healthy value for that parameter than the predefined threshold value.

The measurable physiological parameter may comprise an action potential or pattern of action potentials in one or more nerves of the subject, wherein the action potential or pattern of action potentials is associated with bladder dysfunction. Suitable nerves in which to detect an action potential or pattern of action potentials include a pudendal nerve, a pelvic nerve and/or a hypogastric nerve. In a particular embodiment, the measurable physiological parameter comprises the pattern of action potentials in the pudendal nerve. The measureable physiological parameter may be muscle electromyographic activity, wherein the electromyographic activity is indicative of the level of activity in the muscle. Such activity could typically be measured from the bladder detrusor muscle, the internal urethral sphincter, the external urethral sphincter, and the external anal sphincter.

Treatment of bladder dysfunction, as used herein may be characterised by any one or more of a reduction in number of incontinence episodes, a decrease in urgency of urination, a decrease in frequency of urination, an increase bladder capacity, an increase in bladder voiding efficiency, a decrease in urinary retention, a change in external urethral sphincter (EUS) activity towards that of a healthy individual, and/or a change in the pattern of action potentials or activity of the pelvic nerve, pudendal nerve or hypogastric nerve towards that of a healthy individual. Treatment of bladder function may be characterised by a combination of an increase in bladder capacity during filling periods and an increase in voiding efficiency for voiding periods.

A "neuromodulation apparatus" as used herein is an apparatus configured to modulate the neural activity of a nerve. Neuromodulation devices as described herein comprise at least one transducer capable of effectively applying a signal to a nerve. In those embodiments in which the neuromodulation apparatus is at least partially implanted in the subject, the elements of the apparatus that are to be implanted in the subject are constructed such that they are suitable for such implantation.

As used herein, "implanted" is taken to mean positioned within the subject's body. Partial implantation means that only part of the apparatus is implanted—i.e. only part of the apparatus is positioned within the subject's body, with other elements of the apparatus external to the subject's body. Wholly implanted means that the entire apparatus is positioned within the subject's body. For the avoidance of doubt, the apparatus being "wholly implanted" does not preclude additional elements, independent of the apparatus but in practice useful for its functioning (for example, a remote wireless charging unit or a remote wireless manual override unit), being independently formed and external to the subject's body.

DETAILED DESCRIPTION

In accordance with a first aspect of the invention there is provided an apparatus for stimulating neural activity in a pudendal nerve of a subject, the apparatus comprising: a transducer configured to apply a signal to said nerve; and a controller coupled to the transducer and controlling the signal to be applied by the transducer, such that the controller is configured to cause a first signal to be applied which stimulates neural activity in the pudendal nerve to produce a first physiological response in the subject, and the controller is configured to cause a second signal to applied which stimulates neural activity in the pudendal nerve to produce a second physiological response in the subject, wherein the first and second physiological responses are different.

In certain embodiments, the first and second physiological responses produced in the subject as a result of the first and second signal are each independently selected from one or more of: an increase in bladder capacity, a decrease in the sensation of urgency, a decrease in incontinence, an increase in bladder voiding efficiency, a decrease in urinary retention and/or a change in external urethral sphincter (EUS) activity towards that of a healthy individual. In certain embodiments, the physiological response produced by the first signal is an increase in bladder capacity and the physiological response produced by the second signal is an increase in voiding efficiency.

In certain embodiments, the controller is configured to apply the signal in a phase-specific manner. In certain embodiments, the controller causes the first signal to be applied when the subject is in the storage phase of the micturition cycle and causes the second signal to be applied to trigger the micturition phase. In certain embodiments the controller causes the first signal to be applied when the subject is in the storage phase of the micturition cycle and causes the second signal to be applied when the subject is in the micturition phase of the cycle. In certain such embodiments, the second signal is applied both to trigger micturition and during the subsequent voiding phase. In certain such embodiments, application of the first signal results in an increase in bladder capacity, and application of the second signal results in an increase in voiding efficiency.

In certain embodiments the apparatus comprises a first transducer and a second transducer. In certain such embodiments, the controller is configured to cause the first transducer to apply the first signal, and the second transducer to apply the second signal. In certain embodiments, the controller is configured to cause the first and second transducers to each apply the first and second signals.

In certain embodiments, the first and second transducers may be configured to apply a signal to same pudendal nerve. In certain alternative embodiments, the first and second transducers may be configured such that a signal may be applied bilaterally—that is, the first transducer is configured to apply a signal to the left pudendal nerve, and the second transducer is configured to apply a signal to the right transducer. In such embodiments, the first and second signal may each be configured to apply both the first and second signals, or the first signal may be applied by the first transducer to the left pudendal nerve and the second signal may be applied by the second transducer to the right pudendal nerve.

In the passages below, the described embodiments of the signal apply equally and independently to the first and second signals unless otherwise specified.

In certain embodiments, the signal selectively stimulates neural activity in the sensory fibres of the pudendal nerve. A signal selectively stimulates the neural activity of the sensory fibres of the pudendal nerve if that signal does not modulate the neural activity of the motor fibres of the nerve. In certain alternative embodiments, the signal increases signalling activity of the motor fibres of the nerve, optionally selectively increases the signalling activity of the motor fibres of the nerve.

In certain embodiments, the signal which the transducer is configured to apply is of a modality selected from an electrical signal, an optical signal, an ultrasonic signal, and a thermal signal. That is, each transducer may be configured to apply a different modality of signal. Alternatively, in certain embodiments each transducer is configured to apply the same modality of signal.

In certain embodiments, each transducer may be comprised of one or more electrodes, one or more photon sources, one or more ultrasound transducers, one more sources of heat, or one or more other types of transducer arranged to put the signal into effect.

In certain embodiments, the transducer is an electrode and the signal applied by the transducer is an electrical signal, for example a voltage or current. In certain such embodiments, the transducer is a wire electrode or cuff electrode, for example a bipolar or tripolar cuff electrode.

In certain such embodiments the signal applied comprises a direct current (DC) waveform, or an alternating current (AC) waveform, or both a DC and an AC waveform.

In certain embodiments the signal comprises an AC waveform having a frequency of 0.1-500 Hz, optionally 0.25-100 Hz, optionally 0.5-50 Hz, optionally 1-30 Hz, for example 1, 2, 3, 4, 5, 6, 7, 8, 9, 10, 11, 12, 13, 14, 15, 16, 17, 18, 19, 20, 21, 22, 23, 24, 25, 26, 27, 28. 29, or 30 Hz, optionally 1, 10, 20 or 30 Hz. In certain embodiments the first signal comprises an AC waveform having a frequency of 1-50 Hz, optionally 5-30 Hz, optionally 10-25 Hz, optionally 15-20 Hz, optionally 20 Hz. In certain embodiments the second signal comprises an AC waveform having a frequency of 0.5-50 Hz, optionally 0.5-20 Hz, optionally 1-10 Hz, optionally 1 Hz.

In certain embodiments, the signal is a charge-balanced AC waveform. In certain embodiments, the AC waveform is a biphasic waveform, optionally a charge-balanced biphasic waveform. In certain such embodiments, the waveform may be symmetrical or asymmetrical. In certain such embodiments, each phase of the biphasic waveform has a phase duration from 0.005 ms to 2 ms, optionally 0.01 to 1 ms, optionally 0.05 to 0.5 ms, optionally 0.05 to 0.2 ms, optionally 0.1 ms. In certain embodiments, each phase of a biphasic waveform is of equal duration. In certain alternative embodiments, each phase is of a different duration.

The AC waveform may be selected from sinusoidal, triangular, square or a complex waveform.

Typically, effective induction of the intended physiological effect requires the selection of appropriate stimulation parameters. Stimulation parameters include the stimulation pulse amplitude/intensity, the stimulation pulse duration, and stimulation frequency.

Relative stimulation pulse intensity can be expressed as multiples (0.1, 0.8, 1, 2, 5, etc.) of "T". "T" is the threshold stimulation intensity required to evoke a response. "T" may be the threshold stimulation intensity required to evoke a motor response. In humans, for example, "T" may be defined as the threshold required to evoke a foot or toe twitch, pelvic floor bellowing, pelvic floor contraction (for example anal wink), or a reflex electromyogram (EMG) response in the external urethral sphincter (EUS). Alternatively, "T" may be the threshold stimulation intensity required to evoke a sensory response, for example a response perceived by the patient. Preferably, "T" is the threshold stimulation intensity required to evoke a reflex electromyogram (EMG) response in the external urethral sphincter (EUS).

By way of example, T may be determined as follows: a low frequency electrical signal, typically 1 Hz, is applied and the intensity of stimulation is increased (either by increasing the voltage or the current of the signal, preferably the current) until the pudendal nerve stimulation pulse produces a reflex EMG response in the EUS. This stimulation intensity is designated T. The absolute threshold stimulation intensity may vary across individuals, and subsequent experimental or therapeutic intensities are designated as multiples of T to provide equivalent relative stimulation intensities.

The desired stimulation intensity (i.e. the desired multiple of threshold intensity "T") can be achieved through controlled variation of the current or voltage of the signal, preferably the current.

In certain embodiments the electrical signal has an amplitude value of from 0.1 T to 15.0 T, where T is a threshold obtained through empirical measurement of the threshold for the stimulation signal to evoke a reflex response in the external urethral sphincter or external anal sphincter, following application of stimulus to the pudendal nerve. In certain embodiments, the electrical signal has a T value of 0.1 T-15.0 T, 0.5 T-10 T, 0.5 T-2.0 T, 5.0 T-10 T.

In certain preferred embodiments, the signal is an electrical signal comprising an AC waveform of 400 µA 20 Hz, or 50 µA 1 Hz.

In certain embodiments, the first signal is a high amplitude electrical signal and induces an increase in bladder capacity, and the second signal is a low amplitude electrical signal and induces an increase in voiding efficiency. A high amplitude signal is an electrical signal of 2.0-10 T, optionally 5-10 T, optionally 8-10 T, optionally 2, 3, 4, 5, 6, 7, 8, 9, or 10T and/or of 1-50 Hz. A low amplitude electrical signal is a signal of 0.5-3.0 T, optionally 1-3 T, optionally 2-3 T, optionally 0.5 T, 1 T, 1.5 T, 2 T, 2.5 T, or 3 T and/or of 1-50 Hz. In certain such embodiments, the low amplitude signal has a T value lower than the T value of the high amplitude signal.

In certain embodiments wherein the signal applied by the one or more transducers is a thermal signal, the signal reduces the temperature of the nerve (i.e. cools the nerve). In certain alternative embodiments, the signal increases the temperature of the nerve (i.e. heats the nerve). In certain embodiments, the signal both heats and cools the nerve.

In those embodiments in which the signal applied by the one or more transducers is a thermal signal, at least one of the one or more transducers is configured to apply a thermal signal. In certain such embodiments, all the transducers are configured to apply a thermal signal, optionally the same thermal signal.

In certain embodiments, one or more of the one or more transducers comprise a Peltier element configured to apply a thermal signal, optionally all of the one or more transducers comprise a Peltier element. In certain embodiments, one or more of the one or more transducers comprise a laser diode configured to apply a thermal signal, optionally all of the one or more transducers comprise a laser diode configured to apply a thermal signal (e.g. a diode configured to emit infrared radiation). In certain embodiments, one or more of the one or more transducers comprise an electrically resistive element configured to apply a thermal signal, optionally all of the one or more transducers comprise an electrically resistive element configured to apply a thermal signal.

In certain embodiments the signal applied by the one or more transducers is a mechanical signal, optionally an ultrasonic signal. In certain alternative embodiments, the mechanical signal applied by the one or more transducers is a pressure signal.

In certain embodiments the signal applied by the one or more transducers is an electromagnetic signal, optionally an optical signal. In certain such embodiments, the one or more transducers comprise a laser and/or a light emitting diode configured to apply the optical signal. In some embodiments, the apparatus further comprises a fibre optic interface configured to apply said signal from said one or more of the transducers to said at least one nerve.

In certain embodiments, the apparatus further comprises a detector to detect one or more physiological parameters in the subject. Such a detector may be configured to detect one physiological parameter or a plurality of physiological parameters The detected physiological parameter(s) are selected from nerve activity in the pudendal nerve, nerve activity in the hypogastric nerve, nerve activity in the pelvic nerve, muscle activity in the bladder detrusor muscle, muscle activity in the internal urethral sphincter, muscle activity in the external urethral sphincter, muscle activity in the external anal sphincter, and bladder pressure.

In such embodiments, the controller is coupled to the detector configured to detect a physiological parameter, and causes the first signal to be applied when the physiological parameter is detected to be meeting or exceeding a first predefined threshold value, and causes the second signal to be applied when the physiological parameter is detected to be meeting or exceeding a second predefined threshold value.

It will be appreciated that any two or more of the indicated physiological parameters may be detected in parallel or consecutively. For example, in certain embodiments, the controller is coupled to a detector or detectors configured to detect the pattern of action potentials in the pudendal nerve at the same time as the bladder pressure in the subject.

In addition or as an alternative to a detector, the apparatus may comprise an input element. In such embodiments, the input element allows the subject to enter data regarding their behaviour and/or desires. For example, the input element may allow the subject to enter that they desire to begin bladder voiding (i.e. intend to begin urinating). In such embodiments, the controller is configured to cause a signal to be applied that produces a physiological response appropriate to the data input—for example, in the case of the intention to urinate being indicated, the signal may increase voiding efficiency. By way of further example, the input element may also allow the subject to enter data indicative of behaviour in which storage phase is appropriate (e.g. sleeping or following urination, where it is desirous to promote storage). In response to such data being entered via the input element, the controller causes a signal to be applied that produces a physiological response appropriate for improved storage, for example increased bladder capacity.

The input element may be connected directly to the controller, or be in wireless communication as a remote component, for example a component carried by the subject. Such arrangements and configurations are discussed in further detail below.

According to the invention, stimulation in neural activity as a result of applying the signal is an increase in neural activity in the nerve to which the signal is applied. That is, in such embodiments, application of the signal results in the neural activity in at least the sensory fibres of at least part of the nerve being increased compared to the baseline neural activity in that part of the nerve. In certain embodiments, neural activity is increased across the whole nerve. In certain preferred embodiments, neural activity is selectively stimulated in the sensory fibres of the pudendal nerve to which the signal is applied.

In certain embodiments, the controller causes each signal to be applied for a set time period, such that a stimulation cycle is defined. In such embodiments, the controller is configured to apply the first signal for a first time period and the second signal for a second time period. In certain such embodiments, the first signal produces a physiological response appropriate to aid normal bladder filling and storage (for example increased bladder capacity) and the first time period is of a duration appropriate for a healthy, comfortable storage phase, and the second signal produces a physiological response appropriate to aid voiding (for example, increased voiding efficiency) and the second time period is of a duration appropriate for a healthy voiding phase.

In certain such embodiments, the controller is configured not to cause any signal to be applied for a third time period following the second time period—i.e. after a signal that promotes voiding. An advantage of the controller being so configured is that battery life of the apparatus can be prolonged.

In certain embodiments, the first, second (and third when present) time periods run consecutively and repeat cyclically.

In certain embodiments, the duration of the each time period is independently selected. In certain such embodiments, the duration of each time period is selected from 5 seconds (5 s) to 24 hours (24 h), 30 s to 12 h, 1 min to 12 h, 5 min to 8 h, 5 min to 6 h, 10 min to 6 h, 10 min to 4 h, 30 min to 4 h, 1 h to 4 h. In certain embodiments, the duration of each of the first, second, third and fourth time periods is 5 s, 10 s, 30 s, 60 s, 2 min, 5 min, 10 min, 20 min, 30 min, 40 min, 50 min, 60 min, 90 min, 2 h, 3 h, 4 h, 5 h, 6 h, 7 h, 8 h, 9 h, 10 h, 11 h, 12 h, 13 h, 14 h, 15 h, 16 h, 17 h, 18 h, 19 h, 20 h, 21 h, 22 h, 23 h, 24 h. In certain embodiments, the duration of each time period is selected from 0.05 seconds (0.05 s) to 5 second (5 s), optionally 0.1 s to 2 s, optionally 0.1 s to 1 s, optionally 0.2 s to 0.8 s, optionally 0.3 s to 0.7 s, optionally 0.4 s to 0.6 s, optionally 0.5 s. For example, in certain such embodiments, the signal may be applied for a period of 0.1 ms every 0.5 s (that is, with a period of 0.5 s).

In certain embodiments, the controller is configured to cause the signal to be applied for a specific amount of time per day. In certain such embodiments, each signal may be applied for 10 min, 20 min, 30 min, 40 min, 50 min, 60 min, 90 min, 2 h, 3 h, 4 h, 5 h, 6 h, 7 h, 8 h, 9 h, 10 h, 11 h, 12 h, 13 h, 14 h, 15 h, 16 h, 17 h, 18 h, 19 h, 20 h, 21 h, 22 h, 23 h per day. In certain embodiments, the apparatus is suitable for at least partial implantation into the subject. In certain such embodiments, the apparatus is suitable to be fully implanted in the subject.

In certain embodiments, the apparatus further comprises one or more power supply elements, for example a battery, and/or one or more communication elements.

In a second aspect, the invention provides a method for treating bladder dysfunction in a patient, the method comprising implanting an apparatus according to the first aspect, positioning a transducer of the apparatus in signalling contact with a pudendal nerve of the subject, and activating the apparatus. In such embodiments, the transducer is in signalling contact with the nerve when it is positioned such that a signal can be effectively applied to the nerve. The apparatus is activated when the apparatus is in an operating state such that the signal will be applied as determined by the controller.

In such embodiments, the controller causes the transducer positioned in signalling contact with a pudendal nerve to apply a first signal so as to produce a first physiological response in the subject, and the controller is configured to cause a second signal to applied which stimulates neural activity in the pudendal nerve to produce a second physiological response in the subject, wherein the first and second physiological responses are different.

In certain embodiments, the first signal and second signal are applied to effect phase-specific stimulation. In certain embodiments, the first signal is applied during a filling phase and the second signal is applied to trigger micturition. In certain embodiments the first signal is applied during a filling phase and the second signal applied during a voiding phase. In certain such embodiments, the second signal is applied both to trigger micturition and during the subsequent voiding phase. In certain embodiments, the first and second physiological responses produced in the subject as a result of the first and second signal being applied are each independently selected from one or more of: an increase in bladder capacity, an increase in bladder voiding efficiency, a decrease in urinary retention, a decrease in the sensation of urgency, a decrease in incontinence and/or a change in external urethral sphincter (EUS) activity towards that of a healthy individual. In certain embodiments, the physiological response produced by the first signal is an increase in bladder capacity and the physiological response produced by the second signal is an increase in voiding efficiency.

In certain embodiments, the method comprises implanting an apparatus according to the first aspect having a first transducer and a second transducer, and positioning the transducers bilaterally—that is, one transducer in signalling contact with the left pudendal nerve, and one transducer in signalling contact with the right pudendal nerve. In such embodiments, the controller may cause each transducer to apply either the first signal or the second signal, or may cause the first transducer to apply the first signal and the second transducer to apply the second signal.

In certain embodiments, the method is a method for treating overactive bladder or neurogenic bladder or detrusor hyperactivity with impaired contractility (DHIC).

Implementation of all aspects of the invention (as discussed both above and below) will be further appreciated by reference to FIGS. 2A-2C.

Figure 2A:
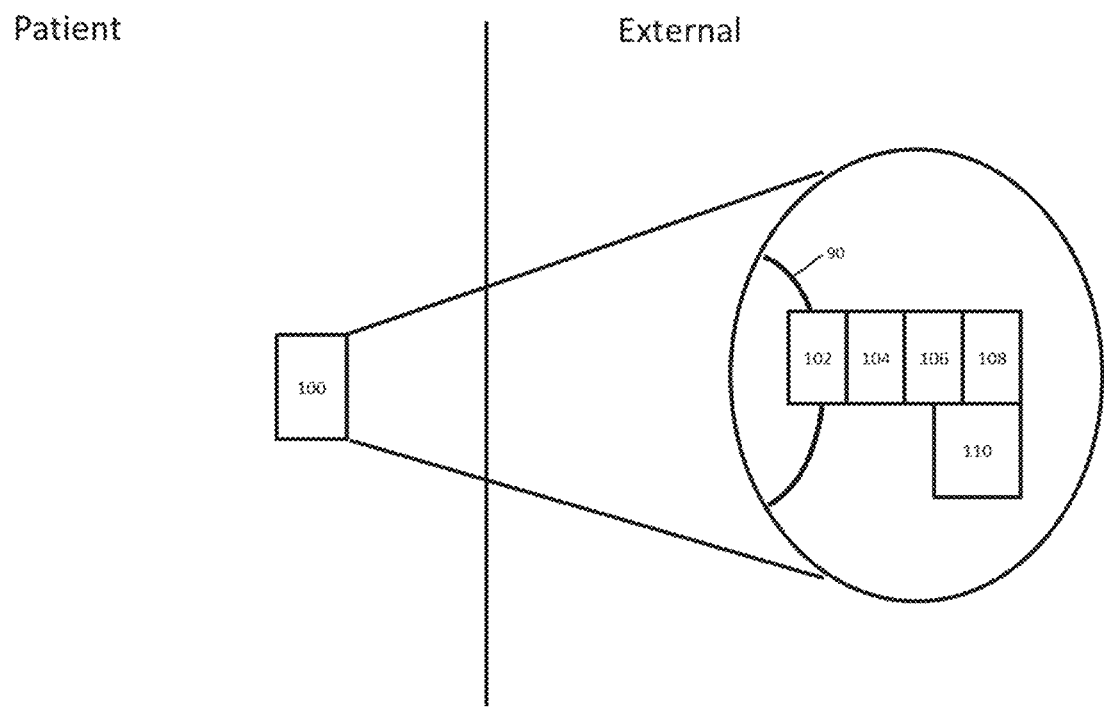
FIGS. 2A-2C: Schematic drawings showing how apparatuses, devices and methods according to the invention can be put into effect.
Figure 2B:
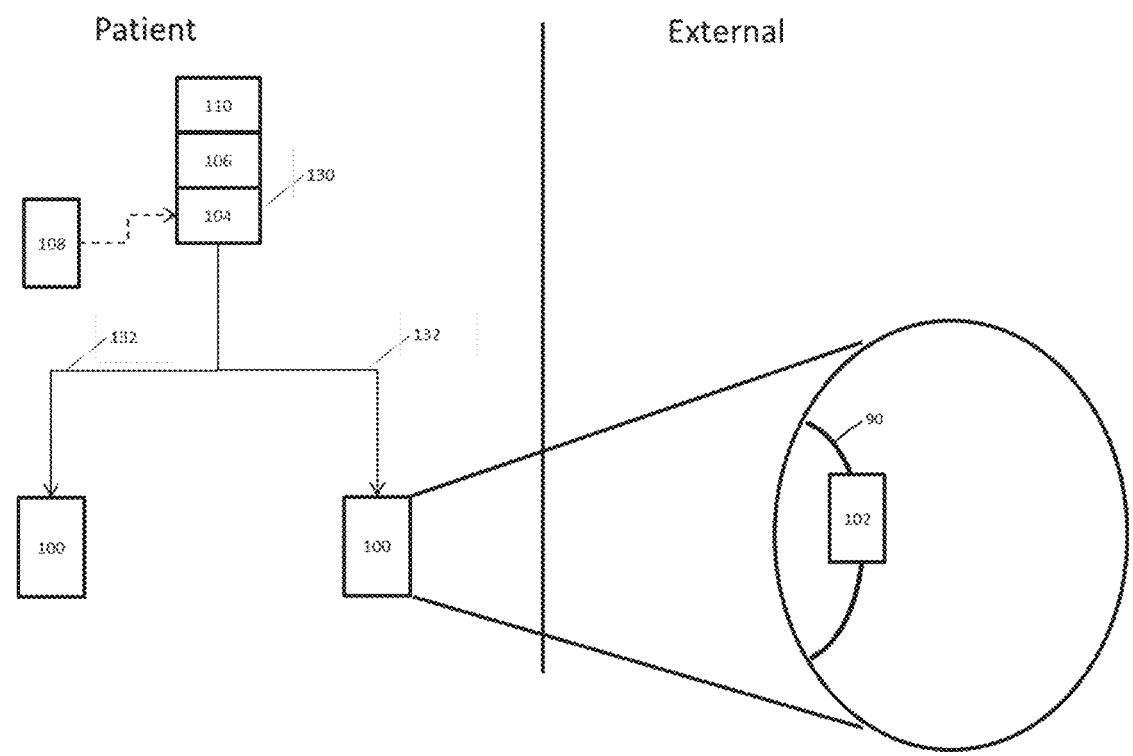
Figure 2C:
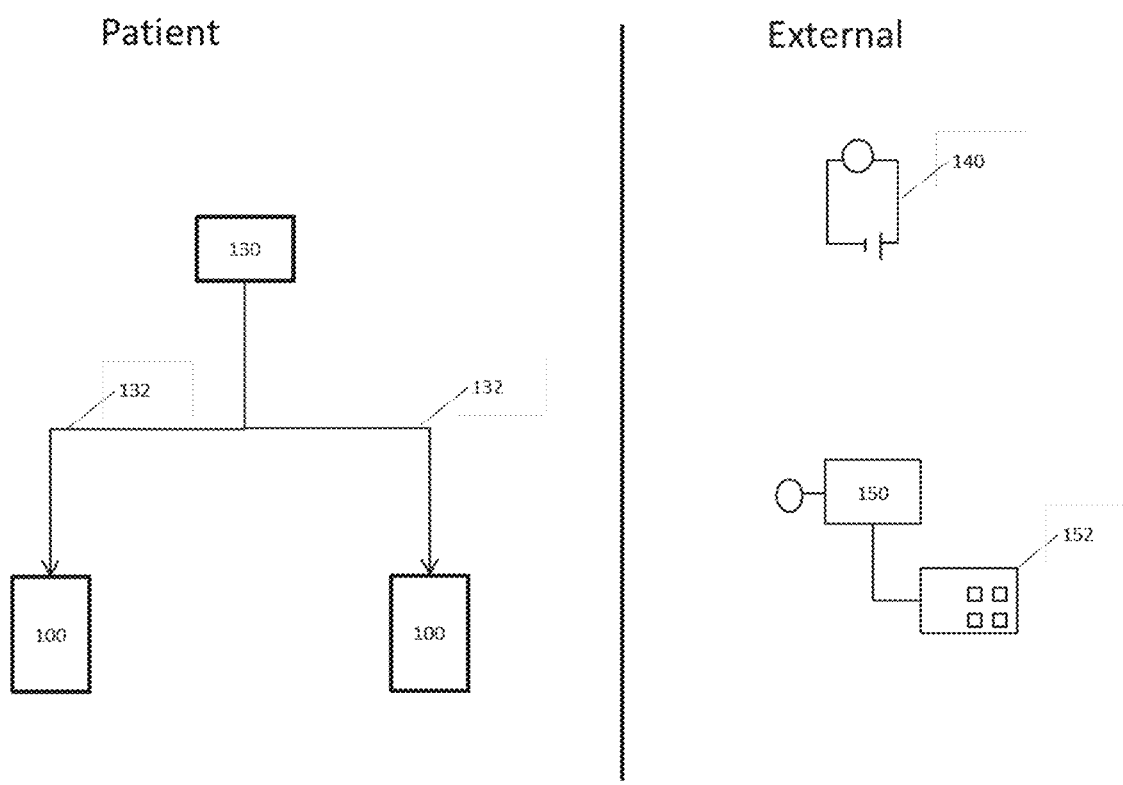

FIGS. 2A-2C show how the invention may be put into effect using one or more neuromodulation apparatuses which are implanted in, located on, or otherwise disposed with respect to a subject in order to carry out any of the various methods described herein. In this way, one or more neuromodulation apparatuses can be used to treat bladder dysfunction in a subject, by modulating neural activity in a pudendal nerve.

In FIG. 2A a separate neuromodulation apparatus 100 is provided for unilateral neuromodulation, although as discussed above and below an apparatus could be provided for bilateral neuromodulation (100, FIG. 2B and 2C). Each such neuromodulation apparatus may be fully or partially implanted in the subject, or otherwise located, so as to provide neuromodulation of the respective nerve or nerves. FIG. 2A also schematically shows in the cutaway components of one of the neuromodulation apparatuses 100, in which the apparatus comprises several elements, components or functions grouped together in a single unit and implanted in the subject. A first such element is a transducer 102 which is shown in proximity to a pudendal nerve 90 of the subject. The apparatus may optionally further comprise further transducers (not shown) implanted proximally to the other pudendal nerve. Alternatively, the other pudendal nerve may be provided with a separate apparatus 100 (not shown). The transducer 102 may be operated by a controller 104. The apparatus may comprise one or more further elements such as a communication element 106, a detector 108, a power supply element 110 and so forth. Each neuromodulation apparatus 100 may operate independently, or may operate in communication with each other, for example using respective communication elements 106.

Each neuromodulation apparatus 100 may carry out the required phase-specific stimulation in response to one or more control signals. Such a control signal may be provided by the controller 104 according to an algorithm independently, in response to output of one or more detector elements 108, and/or in response to communications from one or more external sources (for example an input element) received using the communications element. As discussed herein, the detector(s) could be responsive to a variety of different physiological parameters.

FIG. 2B illustrates some ways in which the apparatus of FIG. 2A may be differently distributed. For example, in FIG. 2B the neuromodulation apparatuses 100 comprise transducers 102 implanted proximally to a pudendal nerve 90, but other elements such as a controller 104, a communication element 106 and a power supply 110 are implemented in a separate control unit 130 which may also be implanted in, or carried by the subject. The control unit 130 then controls the transducers in both of the neuromodulation apparatuses via connections 132 which may for example comprise electrical wires and/or optical fibres for delivering signals and/or power to the transducers.

In the arrangement of FIG. 2B one or more detectors 108 are located separately from the control unit, although one or more such detectors could also or instead be located within the control unit 130 and/or in one or both of the neuromodulation apparatuses 100. The detectors may be used to detect one or more physiological parameters of the subject, and the controller or control unit then causes the transducers to apply the first or second signal in response to the detected parameter(s), for example only when a detected physiological parameter meets or exceeds a predefined threshold value. Physiological parameters which could be detected for such purposes nerve activity in the pudendal nerve, nerve activity in the hypogastric nerve, nerve activity in the pelvic nerve, muscle activity in the bladder detrusor muscle, muscle activity in the internal urethral sphincter, muscle activity in the external urethral sphincter, muscle activity in the external anal sphincter, and bladder pressure.

A variety of other ways in which the various functional elements could be located and grouped into the neuromodulation apparatuses, a control unit 130 and elsewhere are of course possible. For example, one or more sensors of FIG. 2B could be used in the arrangement of FIGS. 2A or 2C or other arrangements.

FIG. 2C illustrates some ways in which some functionality of the apparatus of FIGS. 2A or 2B is provided not implanted in the subject. For example, in FIG. 2C an external power supply 140 is provided which can provide power to implanted elements of the apparatus in ways familiar to the skilled person, and an external controller 150 provides part or all of the functionality of the controller 104, and/or provides other aspects of control of the apparatus, and/or provides data readout from the apparatus, and/or provides a data input element 152. The data input facility could be used by a subject or other operator in various ways, for example to input data relating to the behaviour of the subject and/or their desires (e.g. to begin urination).

Each neuromodulation apparatus may be adapted to carry out the phase-specific stimulation required using one or more physical modes of operation which typically involve applying a first signal and a second signal to a pudendal nerve or subcomponents of a pudendal nerve (e.g. sensory fibres or motor fibres), such signals typically involving a transfer of energy to (or from) the nerve(s). As already discussed, such modes may comprise modulating the nerve or nerves using an electrical signal, an optical signal, an ultrasound or other mechanical signal, a thermal signal, a magnetic or electromagnetic signal, or some other use of energy to carry out the required stimulation. Preferably the modulation comprises selectively stimulating neural activity in the sensory fibres of the nerve or nerves. Alternatively, the signal increases signalling activity of the motor fibres of the nerve, optionally selectively increases the signalling activity of the motor fibres of the nerve. The transducer 90 illustrated in FIG. 2A could be comprised of one or more electrodes, one or more photon sources, one or more ultrasound transducers, one more sources of heat, or one or more other types of transducers arranged to put the required neuromodulation into effect. The neuromodulation apparatus may comprise at least two transducers arranged in order for each to stimulate a different subcomponent of the pudendal nerve, for example a first transducer arranged to stimulate the sensory fibres and a second transducer arranged to stimulate the motor fibres.

The neural modulation apparatus may be arranged to stimulate (i.e. increase or induce) neural activity of a pudendal nerve, by using the transducer(s) to apply a voltage or current, for example a direct current (DC) waveform, or an AC waveform, or both. In such embodiments, the transducer is an electrode, such as a wire electrode or cuff electrode, for example a bipolar or tripolar cuff electrode.

The apparatus may be arranged to use the transducer(s) to apply an electrical signal comprising an AC waveform having a frequency of 0.1-500 Hz, optionally 0.25-100 Hz, optionally 0.5-50 Hz, optionally 1-30 Hz, for example 1, 2, 3, 4, 5, 6, 7, 8, 9, 10, 11, 12, 13, 14, 15, 16, 17, 18, 19, 20, 21, 22, 23, 24, 25, 26, 27, 28. 29, or 30 Hz, optionally 1, 10, 20 or 30 Hz. In certain embodiments the first signal comprises an AC waveform having a frequency of 1-50 Hz, optionally 5-30 Hz, optionally 10-25 Hz, optionally 15-20 Hz, optionally 20 Hz. In certain embodiments the second signal comprises an AC waveform having a frequency of 0.5-50 Hz, optionally 0.5-20 Hz, optionally 1-10 Hz, optionally 1 Hz.

In certain embodiments, the signal is a charge-balanced AC waveform. In certain embodiments, the AC waveform is a biphasic waveform, optionally a charge-balanced biphasic waveform. In certain such embodiments, the waveform may be symmetrical or asymmetrical. In certain such embodiments, each phase of the biphasic waveform has a phase duration from 0.005 ms to 2 ms, optionally 0.01 to 1 ms, optionally 0.05 to 0.5 ms, optionally 0.05 to 0.2 ms, optionally 0.1 ms. In certain embodiments, each phase of a biphasic waveform is of equal duration. In certain alternative embodiments, each phase is of a different duration.

The AC waveform may be selected from sinusoidal, triangular, square or a complex waveform.

In certain embodiments each electrical signal has an amplitude of from 0.1 T to 15 T, where "T" is the intensity of stimulation at which, for a given frequency (typically 1 Hz), a reflex EMG response in the EUS is produced. The skilled person would be readily able to determine the appropriate value of T in any given subject.

In certain embodiments, the electrical signal has a T value of 0.1 T-15.0 T, 0.5 T-10 T, 0.5 T-2.0 T, or 5.0 T-10 T.

In certain embodiments, the first signal is a high amplitude electrical signal and induces an increase in bladder capacity, and the second signal is a low amplitude electrical signal and induces an increase in voiding efficiency. A high amplitude signal is an electrical signal of 2.0-10 T, optionally 5-10 T, optionally 8-10 T, optionally 2, 3, 4, 5, 6, 7, 8, 9, or 10 T and/or of 1-50 Hz. A low amplitude electrical signal is a signal of 0.5-3.0 T, optionally 1-3 T, optionally 2-3 T, optionally 0.5 T, 1 T, 1.5 T, 2T, 2.5 T, or 3 T and/or of 1-50 Hz. In certain such embodiments, the low amplitude signal has a T value lower than the T value of the high amplitude signal.

By way of further example, devices for stimulating nerve activity in the pudendal nerve are described in U.S. Pat. No. 7,571,000 and U.S. Pat. No. 8,396,555, each of which are incorporated herein by reference.

In a third aspect, the invention provides a method of treating bladder dysfunction in a subject by phase-specific stimulation of neural activity in a pudendal nerve of the subject, the method comprising applying a first signal that stimulates neural activity in the pudendal nerve to produce a first physiological response in the subject, and applying a second signal that stimulates neural activity in the pudendal nerve to produce a second physiological response in the subject, wherein the first physiological response and second physiological response are different.

In certain embodiments, the first signal is applied during a filling phase and the second signal is applied to trigger micturition. In certain embodiments the first signal is applied during a filling phase and the second signal is applied during a voiding phase. In certain such embodiments, the second signal is applied both to trigger micturition and during the subsequent voiding phase.

In certain embodiments, the first and second physiological responses produced in the subject as a result of the first and second signal being applied are each selected from one or more of: an increase in bladder capacity, an increase in bladder voiding efficiency, a decrease in urinary retention, a decrease in the sensation of urgency, a decrease in incontinence and/or a change in external urethral sphincter (EUS) activity towards that of a healthy individual. In certain embodiments, the physiological response produced by the first signal is an increase in bladder capacity and the physiological response produced by the second signal is an increase in voiding efficiency.

In certain embodiments, the signals are applied by a neuromodulation apparatus comprising one or more transducers configured to apply the signals.

In certain preferred embodiments the neuromodulation apparatus is at least partially implanted in the subject. In certain preferred embodiments, the neuromodulation apparatus is wholly implanted in the subject. For the avoidance of doubt, the apparatus being "wholly implanted" does not preclude additional elements, independent of the apparatus but in practice useful for its functioning (for example, a remote wireless charging unit or a remote programmer that is used to programme the output of the implanted component or a remote wireless manual override unit), being independently formed and external to the subject's body.

In certain embodiments, the method further comprises detecting one or more physiological parameters in the subject, said parameters being selected from: nerve activity in the pudendal nerve, nerve activity in the hypogastric nerve, nerve activity in the pelvic nerve, muscle activity in the bladder detrusor muscle, muscle activity in the internal urethral sphincter, muscle activity in the external urethral sphincter, muscle activity in the external anal sphincter, and bladder pressure.

In such embodiments, the first signal is applied when a physiological parameter is detected to be meeting or exceeding a first predefined threshold value, and the second signal is applied when a physiological parameter is detected to be meeting or exceeding a second predefined threshold value.

In certain embodiments when the signals are applied by a neuromodulation apparatus, the apparatus further comprises a detector to detect the one or more physiological parameters in the subject. Such a detector may be configured to detect one physiological parameter or a plurality of physiological parameters.

It will be appreciated that any two or more of the indicated physiological parameters may be detected in parallel or consecutively.

In addition or as an alternative to a detector, the apparatus may comprise an input element. In such embodiments of the method, the subject enters data via the input element regarding their behaviour and/or desires to determine when the first and second signals are applied. For example, the subject may enter via the input element that they desire to begin bladder voiding (i.e. intend to begin urinating). In response, the second signal is applied to produce a physiological response appropriate to the intention to commence bladder voiding—for example, the signal may increase voiding efficiency. By way of further example, the subject may enter data via the input element indicative of behaviour in which bladder filling is appropriate (e.g. sleeping or after urination, when it is desirous to promote storage). In response to such data being entered via the input element, the first signal is applied to produce a physiological response appropriate for improved storage, for example increased bladder capacity.

The input element may communicate directly to the transducer(s), or be in wireless communication as a remote component, for example a component carried by the subject. Such arrangements and configurations are discussed in further detail above.

In certain embodiments, the method is applied unilaterally. That is, in such embodiments the signals are applied only to the left or only to the right pudendal nerve. In certain alternative embodiments, the method is applied bilaterally. That is, in such embodiments, a signal is applied to the left and to the right pudendal nerve. In certain such embodiments, the first signal may be applied to the right nerve and the second signal applied to the left nerve, for example. Alternatively, the method may be applied bilaterally such that both the first and second signals are applied to each of the left and right nerves.

In certain embodiments, the signals stimulate neural activity in the sensory fibres of the nerve to which the signal is applied. In certain such embodiments, the signals may selectively stimulate neural activity in the sensory fibres of the nerve to which the signal is applied. A selective stimulation of neural activity of the sensory fibres of the nerve preferentially increases neural signalling in the sensory fibres compared to any stimulation of neural activity in the motor nerve fibres of the pudendal nerve. In certain alternative embodiments, the signal increases signalling activity of the motor fibres of the nerve, optionally selectively increases the signalling activity of the motor fibres of the nerve.

In certain embodiments, the method is a method of treating overactive bladder. In certain embodiments, the method is a method of treating neurogenic bladder. In certain embodiments, the method is a method of treating nocturia. In certain embodiments, the method is a method of treating urinary incontinence. In certain embodiments, the method is a method of treating urine retention. In certain embodiments, the method is a method of treating detrusor hyperactivity with impaired contractility (DHIC). It will be appreciated that the method may treat more than one of these conditions exhibited by a single subject—by way of non-limiting example, the method may treat both nocturia and urine retention in the same subject.

In certain embodiments, the treatment of bladder dysfunction is prophylactic treatment. Prophylactic treatment may be such that it prevents an episode of bladder dysfunction. That is, in subjects known to have bladder dysfunction, the methods of the invention may be used to prevent commencement of an episode of bladder dysfunction, for example by using the method to prevent onset of an episode of incontinence.

In certain embodiments, the treatment of bladder dysfunction is therapeutic treatment. That is, the methods of the invention at least partially restore the bladder function of the subject. For example, methods according to the invention may result in the subject exhibiting levels of urinary retention, incontinence, nocturia, urgency and/or frequency of urination closer to those levels of a healthy subject.

In certain embodiments, treatment of bladder dysfunction is indicated by an improvement in a measurable physiological parameter, for example a reduction in number of incontinence episodes, a reduction in the length and/or severity of incontinence episode(s), a decrease in urgency of urination, a decrease in frequency of urination, an increase in bladder capacity, an increase in bladder voiding efficiency, a decrease in urinary retention, and/or a change in external urethral sphincter (EUS) activity towards that of a healthy individual.

Suitable methods for determining the value for any given parameter would be appreciated by the skilled person.

Each of the first signal and second signal is selected independently of the other, so as to achieve the desired physiological response. The embodiments of the signal may apply to each signal unless specified otherwise and are selected independently.

In certain embodiments, each signal is of a modality selected from an electrical signal, an optical signal, an ultrasonic signal, and a thermal signal.

In those embodiments in which the signals are applied by a neuromodulation apparatus, each transducer of the apparatus may be comprised of one or more electrodes, one or more photon sources, one or more ultrasound transducers, one more sources of heat, or one or more other types of transducer arranged to put each signal into effect.

In certain embodiments, the first and second signals are each electrical signals, for example a voltage or current. In such embodiments when the signal is applied by a neuromodulation apparatus, the one or more transducers of the apparatus are electrodes. In certain such embodiments, the one are more transducers are a wire electrode or cuff electrode, for example a bipolar or tripolar cuff electrode.

In certain embodiments the signals applied comprises a direct current (DC) waveform, or an alternating current (AC) waveform, or both a DC and an AC waveform.

In certain embodiments the signal comprises an AC waveform having a frequency of 0.1-500 Hz, optionally 0.25-100 Hz, optionally 0.5-50 Hz, optionally 1-40 Hz, optionally 1-30Hz, for example 1, 2, 3, 4, 5, 6, 7, 8, 9, 10, 11, 12, 13, 14, 15, 16, 17, 18, 19, 20, 21, 22, 23, 24, 25, 26, 27, 28. 29, or 30 Hz, optionally 1, 10, 20 or 30 Hz, optionally 40 Hz. In certain embodiments the first signal comprises an AC waveform having a frequency of 1-50 Hz, optionally 5-30 Hz, optionally 10-25 Hz, optionally 15-20 Hz, optionally 20 Hz. In certain embodiments the second signal comprises an AC waveform having a frequency of 0.5-50 Hz, optionally 0.5-20 Hz, optionally 1-10 Hz, optionally 1 Hz.

In certain embodiments, the signal is a charge-balanced AC waveform. In certain embodiments, the AC waveform is a biphasic waveform, optionally a charge-balanced biphasic waveform. In certain such embodiments, the waveform may be symmetrical or asymmetrical. In certain such embodiments, each phase of the biphasic waveform has a phase duration from 0.005 ms to 2 ms, optionally 0.01 to 1 ms, optionally 0.05 to 0.5 ms, optionally 0.05 to 0.2 ms, optionally 0.1 ms. In certain embodiments, each phase of a biphasic waveform is of equal duration. In certain alternative embodiments, each phase is of a different duration.

The AC waveform may be selected from sinusoidal, triangular, square or a complex waveform.

Typically, effective induction of the intended physiological effect requires the selection of appropriate stimulation parameters. Stimulation parameters include the stimulation pulse amplitude/intensity, the stimulation pulse duration, and stimulation frequency.

Relative stimulation pulse intensity can be expressed as multiples (0.1, 0.8, 1, 2, 5, etc.) of "T". "T" is the threshold stimulation intensity required to evoke a response. "T" may be the threshold stimulation intensity required to evoke a motor response. In humans, for example, "T" may be defined as the threshold required to evoke a foot or toe twitch, pelvic floor bellowing, pelvic floor contraction (for example anal wink), or a reflex electromyogram (EMG) response in the external urethral sphincter (EUS). Alternatively, "T" may be the threshold stimulation intensity required to evoke a sensory response, for example a response perceived by the patient. Preferably, "T" is the threshold stimulation intensity required to evoke a reflex electromyogram (EMG) response in the external urethral sphincter (EUS).

By way of example, T may be determined as follows: a low frequency electrical signal, typically 1 Hz, is applied and the intensity of stimulation is increased (either by increasing the voltage or the current of the signal, preferably the current) until the pudendal nerve stimulation pulse produces a reflex EMG response in the EUS. This stimulation intensity is designated T. The absolute threshold stimulation intensity may vary across individuals, and subsequent experimental or therapeutic intensities are designated as multiples of T to provide equivalent relative stimulation intensities.

The desired stimulation intensity (i.e. the desired multiple of threshold intensity "T") can be achieved through controlled variation of the current or voltage of the signal, preferably the current.

In certain embodiments the electrical signal has an amplitude value of from 0.1 T to 15.0 T, where T is a threshold obtained through empirical measurement of the threshold for the stimulation signal to evoke a reflex response in the external urethral sphincter or external anal sphincter, following application of stimulus to the pudendal nerve. In certain embodiments, the electrical signal has a T value of 0.1 T-15.0 T, 0.5 T-10 T, 0.5 T-2.0 T, 5.0 T-10 T.

In certain embodiments, the first signal is a high amplitude electrical signal and induces an increase in bladder capacity, and the second signal is a low amplitude electrical signal and induces an increase in voiding efficiency. A high amplitude signal is an electrical signal of 2.0-10 T, optionally 5-10 T, optionally 8-10 T, optionally 2, 3, 4, 5, 6, 7, 8, 9, or 10 T and/or of 1-50 Hz. A low amplitude electrical signal is a signal of 0.5-3.0 T, optionally 1-3 T, optionally 2-3 T, optionally 0.5 T, 1 T, 1.5 T, 2 T, 2.5 T, or 3 T and/or of 1-50 Hz. In certain such embodiments, the low amplitude signal has a T value lower than the T value of the high amplitude signal.

In certain preferred embodiments, the signal is an electrical signal comprising an AC waveform of 400 µA 20 Hz, or 50 µA 1 Hz.

In certain embodiments wherein the signal applied is a thermal signal, the signal reduces the temperature of the nerve (i.e. cools the nerve). In certain alternative embodiments, the signal increases the temperature of the nerve (i.e. heats the nerve). In certain embodiments, the signal both heats and cools the nerve.

In those embodiments in which the signal applied is a thermal signal and is applied by a neuromodulation device, at least one of the one or more transducers is configured to apply a thermal signal. In certain such embodiments, all the transducers are configured to apply a thermal signal, optionally the same thermal signal.

In certain embodiments, one or more of the one or more transducers comprise a Peltier element configured to apply a thermal signal, optionally each of the one or more transducers comprises a Peltier element. In certain embodiments, one or more of the one or more transducers comprise a laser diode configured to apply a thermal signal, optionally each of the one or more transducers comprises a laser diode configured to apply a thermal signal (e.g. a diode configured to emit infrared radiation). In certain embodiments, one or more of the one or more transducers comprise an electrically resistive element configured to apply a thermal signal, optionally all of the one or more transducers comprise an electrically resistive element configured to apply a thermal signal.

In certain embodiments the signal applied is a mechanical signal, optionally an ultrasonic signal. In certain alternative embodiments, the mechanical signal applied is a pressure signal.

In certain embodiments the signal applied is an electromagnetic signal, optionally an optical signal. In certain such embodiments when the signals are applied by a neuromodulation device, the one or more transducers comprise a laser and/or a light emitting diode configured to apply the optical signal. In some embodiments, the apparatus further comprises a fibre optic interface configured to apply said signal from said one or more of the transducers to the nerve.

In certain embodiments, each signal is applied for a set time period, such that a stimulation cycle is defined. In such embodiments, the first signal is applied for a first time period and the second signal for a second time period. In certain such embodiments, the first time period is of a duration appropriate for a healthy, comfortable storage phase, and the second time period is of a duration appropriate for a healthy voiding phase.

In certain embodiments when the signals are applied by a neuromodulation apparatus, a third time period follows the second time period during which no signal is applied. An advantage of not applying a signal for a period of time following voiding is that battery life of the apparatus can be prolonged.

In certain embodiments, the first, second (and third when present) time periods run consecutively and repeat cyclically.

In certain embodiments, the duration of the each time period is independently selected. In certain such embodiments, the duration of each time period is selected from 5 seconds (5 s) to 24 hours (24 h), 30 s to 12 h, 1 min to 12 h, 5 min to 8 h, 5 min to 6 h, 10 min to 6 h, 10 min to 4 h, 30 min to 4 h, 1 h to 4 h. In certain embodiments, the duration of each of the first, second, third and fourth time periods is 5 s, 10 s, 30 s, 60 s, 2 min, 5 min, 10 min, 20 min, 30 min, 40 min, 50 min, 60 min, 90 min, 2 h, 3 h, 4 h, 5 h, 6 h, 7 h, 8 h, 9 h, 10 h, 11 h, 12 h, 13 h, 14 h, 15 h, 16 h, 17 h, 18 h, 19 h, 20 h, 21 h, 22 h, 23 h, 24 h. In certain embodiments, the duration of each time period is selected from 0.05 seconds (0.05 s) to 5 second (5 s), optionally 0.1 s to 2 s, optionally 0.1 s to 1 s, optionally 0.2 s to 0.8 s, optionally 0.3 s to 0.7 s, optionally 0.4 s to 0.6 s, optionally 0.5 s. For example, in certain such embodiments, the signal may be applied for a period of 0.1 ms every 0.5 s (that is, with a period of 0.5 s).

In certain embodiments, the controller is configured to cause the signal to be applied for a specific amount of time per day. In certain such embodiments, each signal may be applied for 10 min, 20 min, 30 min, 40 min, 50 min, 60 min, 90 min, 2 h, 3 h, 4 h, 5 h, 6 h, 7 h, 8 h, 9 h, 10 h, 11 h, 12 h, 13 h, 14 h, 15 h, 16 h, 17 h, 18 h, 19 h, 20 h, 21 h, 22 h, 23 h per day. In certain such embodiments, each signal is caused to be applied continuously for the specified amount of time. In certain alternative such embodiments, each signal may be applied discontinuously across the day, provided the total time of application amounts to the specified time.

In certain embodiments wherein the signal is applied intermittently, each signal is applied for a specific amount of time per day. In certain such embodiments, the signal is applied for 10 min, 20 min, 30 min, 40 min, 50 min, 60 min, 90 min, 2 h, 3 h, 4 h, 5 h, 6 h, 7 h, 8 h, 9 h, 10 h, 11 h, 12 h, 13 h, 14 h, 15 h, 16 h, 17 h, 18 h, 19 h, 20 h, 21 h, 22 h, 23 h per day.

In certain embodiments wherein the modulation is bilateral, each signal is applied by a single neuromodulation apparatus. In certain alternative embodiments, the left-side signal(s) is applied by one neuromodulation apparatus and right-side signal(s) is applied by another neuromodulation apparatus.

In a fourth aspect, the invention provides use of a neuromodulation apparatus for treating bladder dysfunction in a subject by phase-specific stimulation of neural activity in a pudendal nerve of the subject.

In a fifth aspect the invention provides a neuromodulation system, the system comprising a plurality of apparatuses according to the first aspect. In such a system, each apparatus may be arranged to communicate with at least one other apparatus, optionally all apparatuses in the system. In certain embodiments, the system is arranged such that, in use, the apparatuses are positioned to bilaterally stimulate the pudendal nerves of a patient.

In such embodiments, the system may further comprise additional components arranged to communicate with the apparatuses of the system, for example a processor, a data input facility, and/or a data display module. In certain such embodiments, the system further comprises a processor. In certain such embodiments, the processor is comprised within a mobile device (for example a smart phone) or computer.

In a sixth aspect, the invention provides a pharmaceutical composition comprising a compound for treating bladder dysfunction, for use in a method of treating bladder dysfunction in a subject, wherein the method is a method according to the second aspect of the invention or according to the third aspect of the invention, the method further comprising the step of administering an effective amount of the pharmaceutical composition to the subject. It is a preferred embodiment that the pharmaceutical composition is for use in a method of treating bladder dysfunction wherein the method comprises applying a signal to a part or all of a pudendal nerve of said patient to stimulate the neural activity of said nerve in the patient, the signal being applied by a neuromodulation apparatus.

In a seventh aspect, the invention provides a pharmaceutical composition comprising a compound for treating bladder dysfunction, for use in treating bladder dysfunction in a subject, the subject having an apparatus according to the first aspect implanted. That is, the pharmaceutical composition is for use in treating a subject that has had an apparatus as described according to the first aspect implanted. The skilled person will appreciate that the apparatus has been implanted in a manner suitable for the apparatus to operate as described. Use of such a pharmaceutical composition in a patient having an apparatus according to the first aspect implanted will be particularly effective as it permits a cumulative or synergistic effect as a result of the combination of the compound for treating bladder dysfunction and apparatus operating in combination.

In certain embodiments of the sixth or seventh aspect, the compound for treating bladder dysfunction is selected from an antimuscarinic compound and a β-adrenergic receptor agonist, optionally a β3-adrenergic receptor agonist. In certain embodiments, the antimuscarinic compound is selected from darifenacin, hyoscyamine, oxybutynin, tolterodine, solifenacin, trospium, or fesoterodine. In certain embodiments, the β-adrenergic receptor agonist is a β3-adrenergic receptor agonist, for example mirabegron. In certain embodiments, the pharmaceutical composition is for use in treating OAB.

In certain embodiments, the pharmaceutical composition may comprise a pharmaceutical carrier and, dispersed therein, a therapeutically effective amount of the compounds for treating bladder dysfunction. The composition may be solid or liquid. The pharmaceutical carrier is generally chosen based on the type of administration being used and the pharmaceutical carrier may for example be solid or liquid. The compounds of the invention may be in the same phase or in a different phase than the pharmaceutical carrier.

Pharmaceutical compositions may be formulated according to their particular use and purpose by mixing, for example, excipient, binding agent, lubricant, disintegrating agent, coating material, emulsifier, suspending agent, solvent, stabilizer, absorption enhancer and/or ointment base. The composition may be suitable for oral, injectable, rectal or topical administration.

For example, the pharmaceutical composition may be administered orally, such as in the form of tablets, coated tablets, hard or soft gelatine capsules, solutions, emulsions, or suspensions. Administration can also be carried out rectally, for example using suppositories, locally or percutaneously, for example using ointments, creams, gels or solution, or parenterally, for example using injectable solutions.

For the preparation of tablets, coated tablets or hard gelatine capsules, the compounds for treating bladder dysfunction may be admixed with pharmaceutically inert, inorganic or organic excipients. Examples of suitable excipients include lactose, maize starch or derivatives thereof, talc or stearic acid or salts thereof. Suitable excipients for use with soft gelatine capsules include, for example, vegetable oils, waxes, fats and semi-solid or liquid polyols.

For the preparation of solutions and syrups, excipients include, for example, water, polyols, saccharose, invert sugar and glucose. For injectable solutions, excipients include, for example, water, alcohols, polyols, glycerine and vegetable oil. For suppositories and for local and percutaneous application, excipients include, for example, natural or hardened oils, waxes, fats and semi-solid or liquid polyols.

The pharmaceutical compositions may also contain preserving agents, solublizing agents, stabilizing agents, wetting agents, emulsifiers, sweeteners, colorants, odorants, buffers, coating agents and/or antioxidants.

Thus, a pharmaceutical formulation for oral administration may, for example, be granule, tablet, sugar coated tablet, capsule, pill, suspension or emulsion. For parenteral injection for, for example, intravenous, intramuscular or subcutaneous use, a sterile aqueous solution may be provided that may contain other substances including, for example, salts and/or glucose to make to solution isotonic. The compound may also be administered in the form of a suppository or pessary, or may be applied topically in the form of a lotion, solution, cream, ointment or dusting powder.

In a preferred embodiment of all aspects of the invention, the subject or subject is a mammal, more preferably a human. In certain embodiments, the subject or subject is suffering from bladder dysfunction.

The foregoing detailed description has been provided by way of explanation and illustration, and is not intended to limit the scope of the appended claims. Many variations in the presently preferred embodiments illustrated herein will be apparent to one of ordinary skill in the art, and remain within the scope of the appended claims and their equivalents.

EXAMPLES

Example 1

In the following examples, an accepted animal model of bladder dysfunction was used: the PGE2 (prostoglandin E2) model, in which installation of PGE2 into rats induces a hyperactive bladder response. In addition, a cat model of bladder dysfunction was used. Cats exhibit a urinary function similar to humans, and thus can represent a representative model for human disease.

Methodology

Acute experiments were conducted in urethane (1.2 g/kg, SC) anesthetized female Wistar rats using in vivo cystometry (CMG). A PE-90 catheter was placed to measure bladder pressure and for intravesical infusion of saline and PGE2 (100 µM). Bipolar electrodes were placed on the external urethral sphincter (EUS) to measure electromyographic (EMG) activity and a bipolar nerve cuff electrode was placed on the sensory branch of the pudendal nerve for stimulation.

Figure 3:
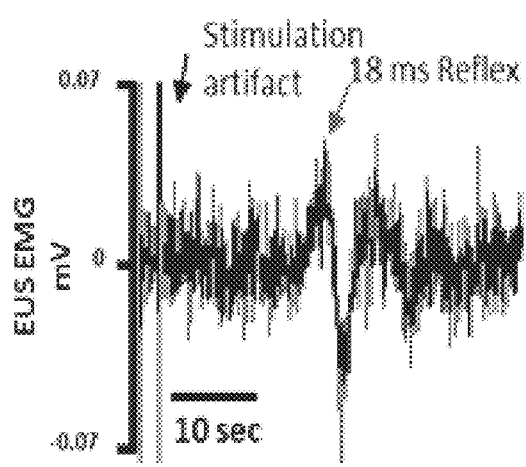
FIG. 3: Electromyographic (EMG) response measured from the external urethral sphincter in response to electrical stimulation of the pudendal nerve showing the reflex response used to determine stimulation intensity threshold (T).

In a subset of trials after PGE2 infusion, electrical stimulation of the sensory branch of the pudendal nerve was delivered at different amplitudes (0.5-10 x EUS reflex threshold, T) and frequencies (1-50 Hz). T may be determined as follows: a low frequency electrical signal, typically 1 Hz, is applied and the intensity of stimulation is increased (either by increasing the voltage or the current of the signal, preferably the current) until the pudendal nerve stimulation pulse produces a reflex EMG response in the EUS. This stimulation intensity is designated T. FIG. 3 shows the reflex response in EUS EMG activity used to determine T.

Results

Figure 5A:
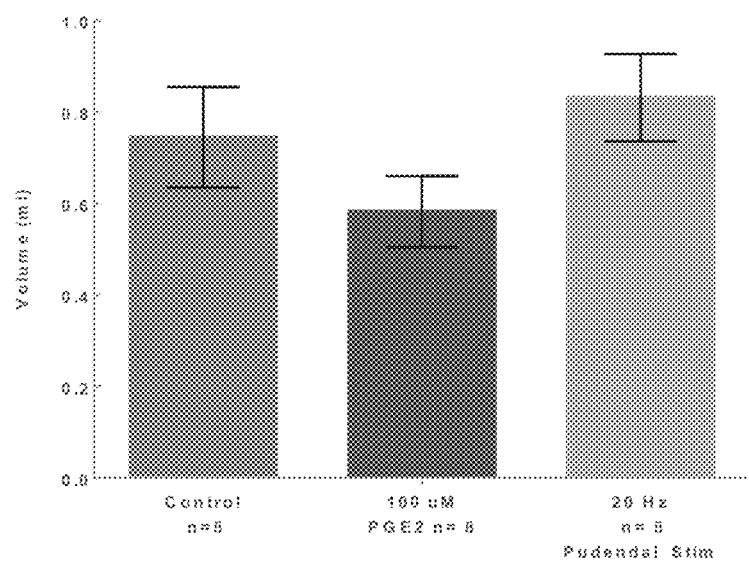
FIGS. 5A-5B: Summary of changes in bladder capacity (FIG. 5A) and voiding efficiency (FIG. 5B) in urethane anesthetized rats following installation of PGE2 in the bladder and during the delivery of "high intensity" pudendal nerve stimulation. PGE2 reduces bladder capacity and this effect is reversed by "high intensity" pudendal nerve stimulation. However "high intensity" pudendal nerve stimulation reduced voiding efficiency.

As shown in FIG. 4, a "high amplitude" stimulation of the pudendal nerve (200 µA 20 Hz, FIG. 4A, right trace) resulted in an improved bladder capacity in PGE2 rats compared to control PGE2 rats (FIG. 4A, left trace). The improved bladder capacity is indicated by a slower rate of increase in bladder pressure, as well as a greater absolute bladder pressure before micturition (micturition being indicated by the sharp spike in bladder pressure). The increase in bladder capacity is further shown in FIG. 5A, where high amplitude stimulation (right hand bar) resulted in a clear increase in bladder volume compared to unstimulated PGE2 rats (central bar) and to control rats (left hand bar).

Figure 5B:
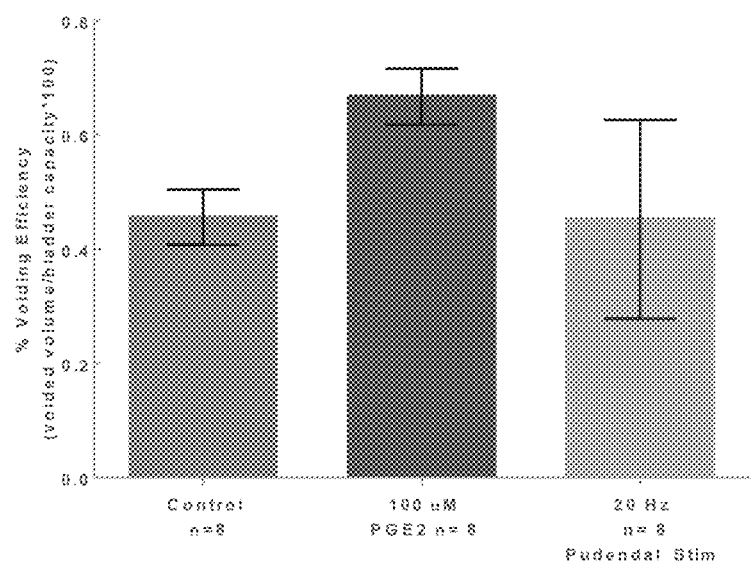

FIG. 4B shows that high amplitude stimulation affects external urethral sphincter (EUS) EMG activity (right trace) compared to PGE2 rats in which no high amplitude stimulation is applied (left trace). This effect resulted in a decrease in voiding efficiency, as shown in FIG. 5B.

As both effective bladder capacity and voiding efficiency are important for healthy bladder activity, it was investigated whether a phase-specific stimulation protocol could improve both bladder capacity and voiding efficiency in PGE2 rats. In particular, it was investigated whether both bladder capacity and voiding efficiency could be improved using a high amplitude stimulation during filling phase, and a low amplitude stimulation during voiding phase.

Figure 6A:
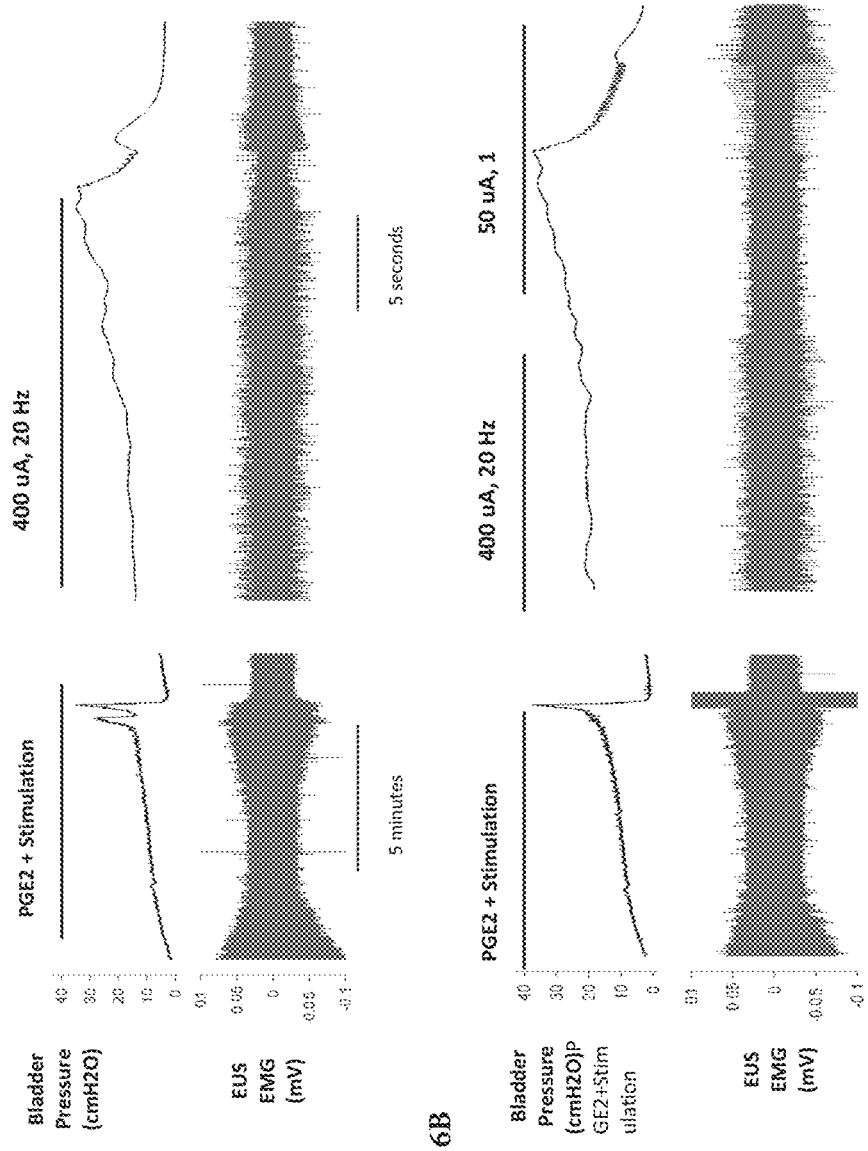
FIGS. 6A-6B: State-dependent switching of stimulation intensity increases both bladder capacity and voiding efficiency in urethane anesthetized rats following installation of PGE2 in the bladder.
Figure 6B:
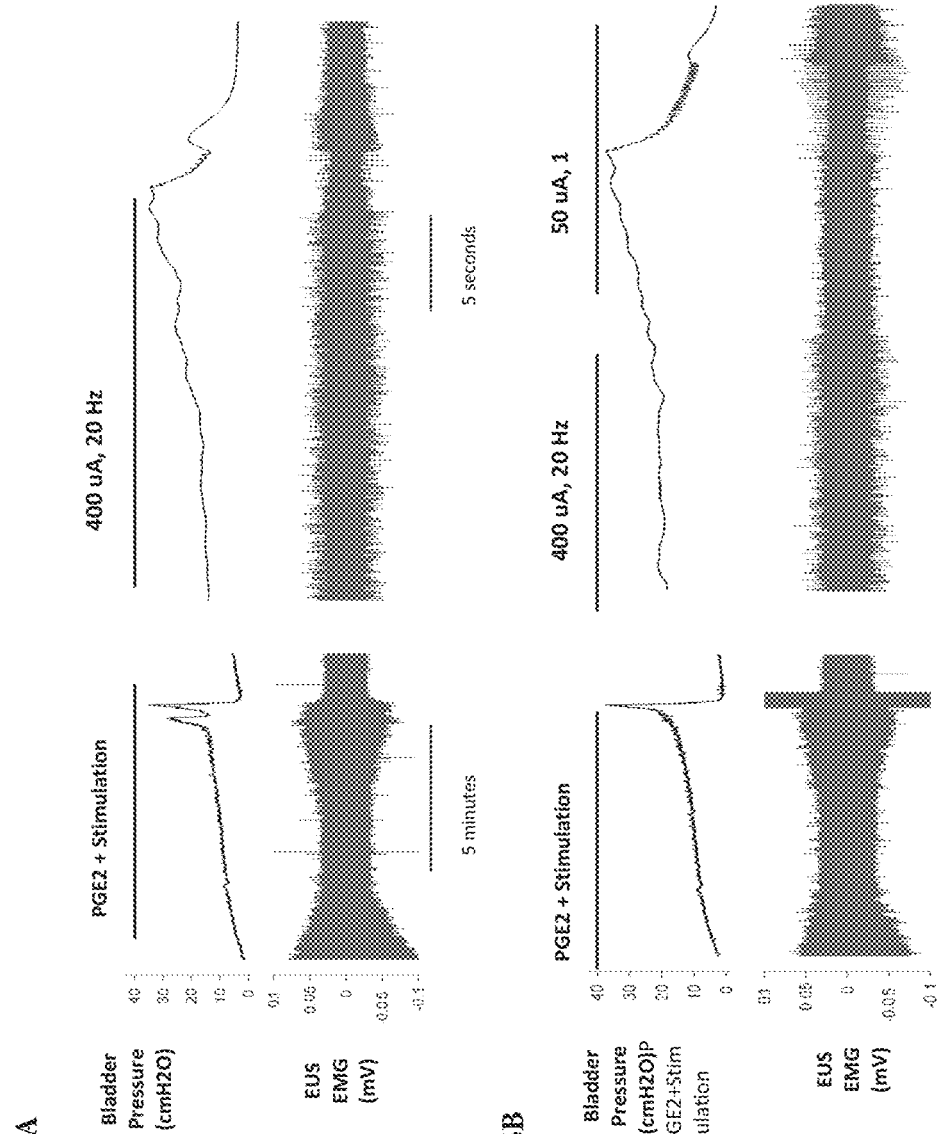
Figure 7A:
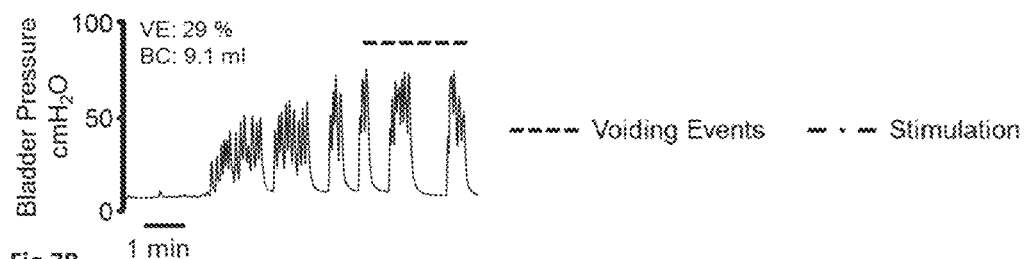
FIGS. 7A-7D: Example cystometrogram trials in cats during distention evoked voiding (FIG. 7A) and distention evoked voiding with unilateral compound pudendal stimulation (FIGS. 7B-7D).
Figure 7B:
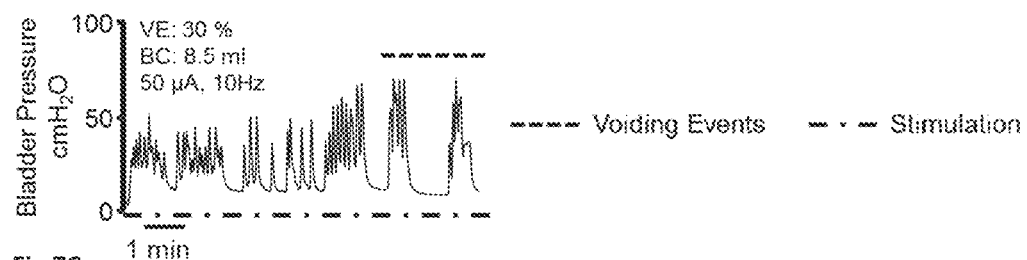
Figure 7C:
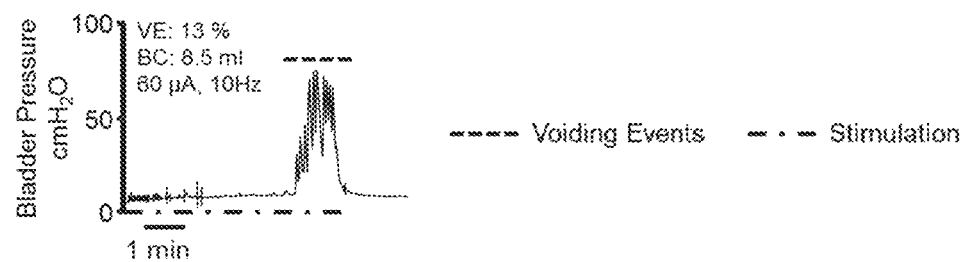
Figure 7D:
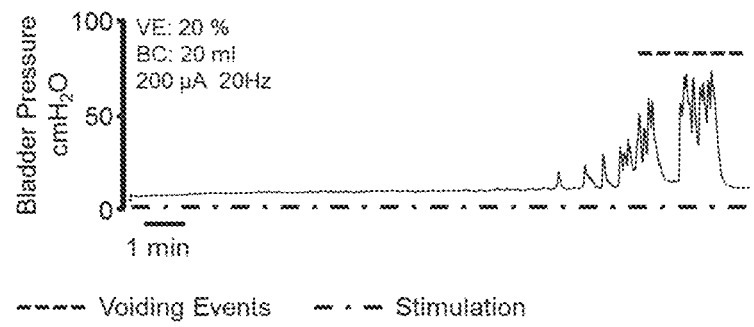

FIG. 6 shows a comparison of high amplitude stimulation (400 µA 20 Hz) alone (A) and phase-specific stimulation (i.e. high amplitude stimulation (400 µA 20 Hz) during filling phase and low amplitude stimulation (50 µA 1 Hz) during voiding phase; FIG. 6B). For high amplitude stimulation only (FIG. 6A), stimulation was stopped just before commencement of the voiding phase. For phase-specific stimulation, instead of stopping stimulation just before voiding phase, the stimulation was switched from high amplitude to low amplitude stimulation. The left hand traces show each parameter over a broader time period, and therefore lower resolution, whilst the right hand traces show each parameter over a shorter time period, therefore providing a higher resolution.

With no stimulation, bladder capacity was 0.49 ml and voiding efficiency was 56% (data not shown).

The high amplitude pudendal nerve stimulation alone (FIG. 6A) increased bladder capacity to 0.63 ml, but had only a marginal effect on voiding efficiency (=62%). Phase-specific switching of stimulation amplitude from high during the filling phase to low during the voiding phase increased both bladder capacity (=0.67 ml) and voiding efficiency (=82%) (FIG. 6B).

FIG. 7 shows data from a cystometrogram in a cat model in which the effect of low amplitude stimulation (B and C), and high amplitude stimulation (D) on bladder pressure, bladder capacity and voiding efficiency is compared to an unstimulated control (A). Low amplitude stimulation had little effect on bladder capacity or voiding efficiency (with a possible reduction in voiding efficiency observed in (C)). However, high amplitude stimulation greatly improved bladder capacity (D), in accordance with data obtained from the rat model. High amplitude signalling did not significantly alter voiding efficiency and, due to the increased bladder capacity, this could lead to issues with undue urine retention. This further supports the rat data and the need for a phase-specific stimulation approach in order to also improve voiding efficiency.

FIG. 8 shows further data from the cat model in which voiding efficiency as a result of low amplitude stimulation (D, E, F) is compared with voiding efficiency in control animals (A, B, C).

Animals in the intervention group were stimulated during voiding phase with bursts of 40 Hz pulses at amplitude to evoke robust contraction of the external urethral sphincter (0.25-0.9 mA) for 100 ms, with a period of 0.5 s for each burst (FIG. 8G). These data clearly show increased voiding efficiency as a result of applying the low amplitude signal. Used in combination with the high amplitude signal to improve bladder capacity during filling, these data support the use of phase-specific stimulation to treat bladder dysfunction.

Figure 9A:
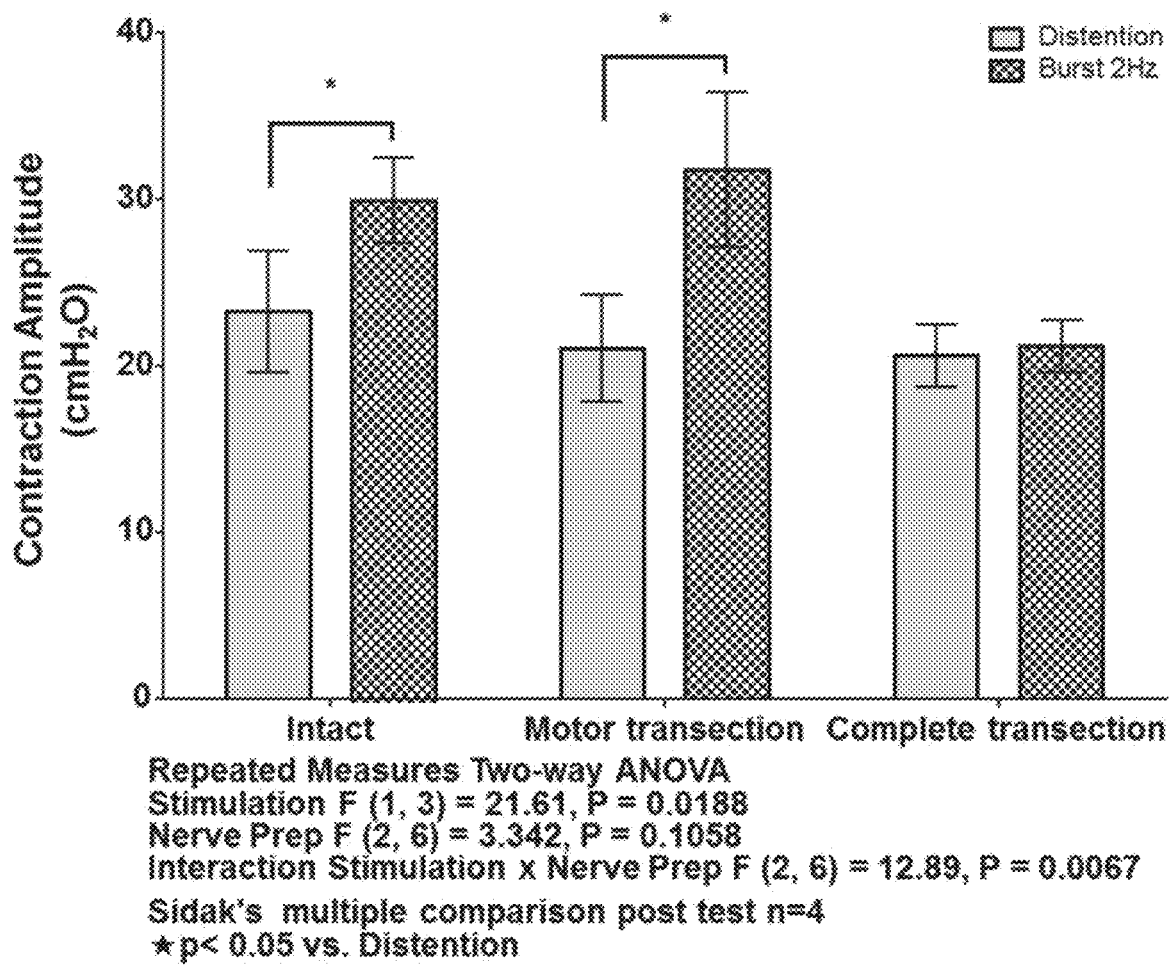
FIGS. 9A-9C: Average bladder contraction amplitude (FIG. 9A), bladder contraction area under the curve (AUC) (FIG. 9B), and voiding efficiency (FIG. 9C) in cat during voiding trials between distention evoked control and pudendal somatic motor branch (DPeriN) 2 Hz burst stimulation during intact, motor transection, and complete (sensory and motor) transection conditions.
Figure 9B:
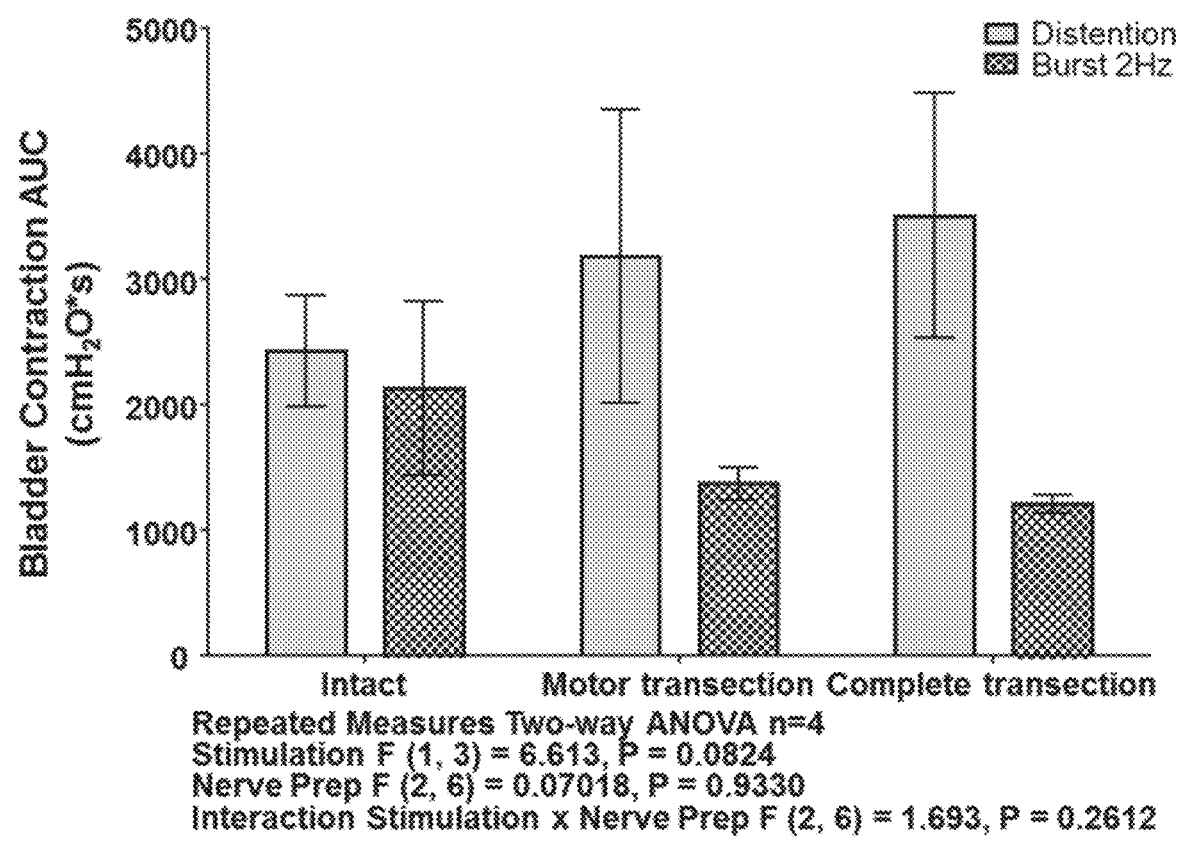
Figure 9C:
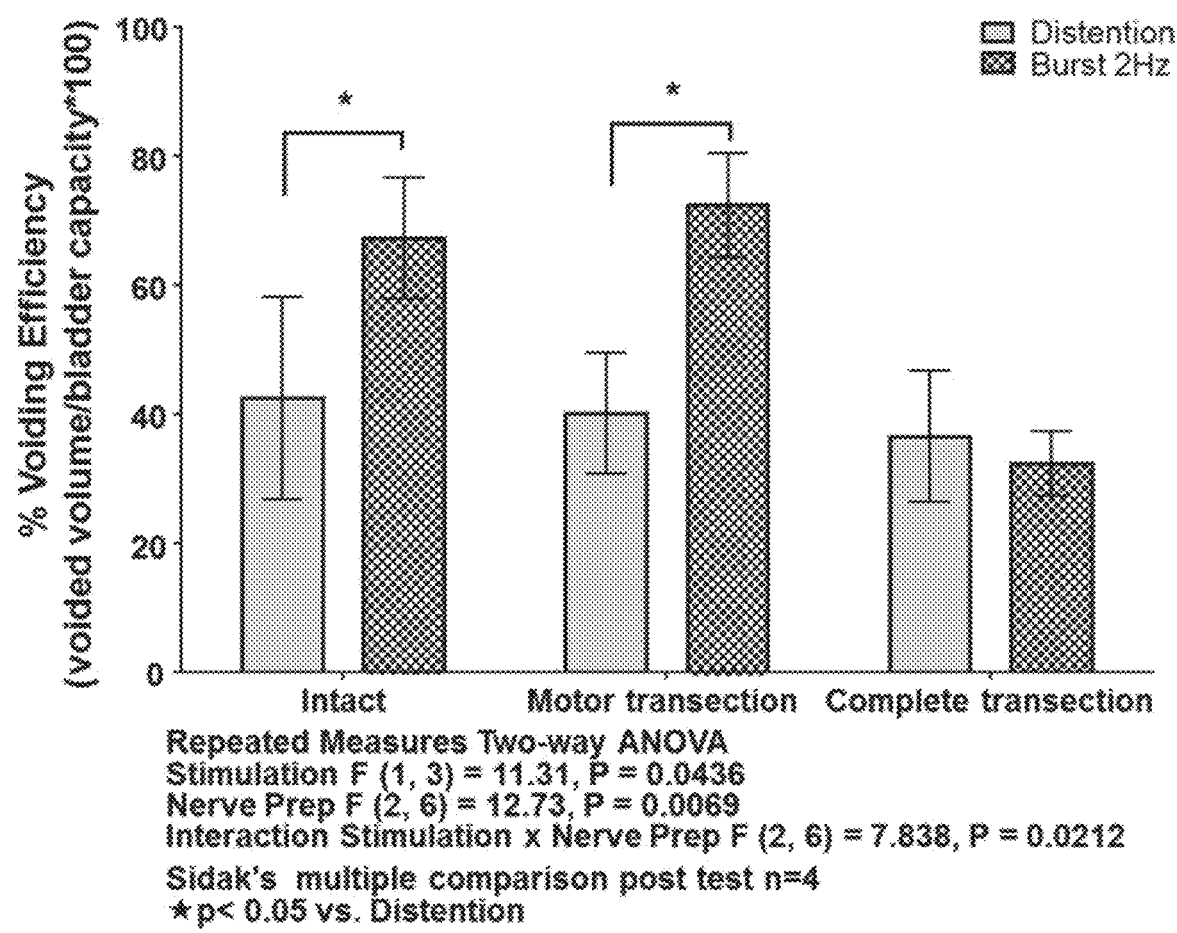

FIG. 9 shows the effect of transection of the pudendal motor fibres only or transection of both sensory and motor fibres on the changes in bladder contraction amplitude and voiding efficiency induced by low amplitude stimulation of the deep perineal branch of the pudendal nerve that innervates the external urethral sphincter. FIGS. 9A and 9C show that stimulation with the entire nerve intact or following transection proximal to stimulation of the motor fibres exhibit improved bladder contraction and improved voiding efficiency, but that this is lost when both sensory and motor fibres are transected. This indicates that the improved voiding is mediated by physiological activation of pudendal sensory fibres occurring as a result of the motor contractions generated in the external urethral sphincter by motor fibre stimulation. FIG. 9B shows that stimulation of intact or transected pudendal nerves does not achieve a statistically significant effect on bladder contraction AUC.

These experiments demonstrate that phase specific stimulation of the pudendal nerve is able to provide improved bladder activity across the whole bladder activity cycle. In particular, phase-specific pudendal nerve stimulation is able to induce improved bladder capacity and improved voiding efficiency.

The invention claimed is:

1. An apparatus for stimulating neural activity in a pudendal nerve of a subject, the apparatus comprising:
   at least one transducer configured to apply a signal to said nerve; and
   a controller coupled to the transducer(s) and controlling the signal to be applied by the transducer(s),
   wherein the controller is configured to cause at least one transducer to apply a first signal that stimulates neural activity in the pudendal nerve to produce a first physiological response in the subject, and the controller is configured to cause at least one transducer to apply a second signal that stimulates neural activity in the pudendal nerve to produce a second physiological response in the subject, wherein the first physiological response and second physiological response are different, and wherein the first signal is timed to be applied during a filling phase and the second signal is timed to be applied during a voiding phase.

2. The apparatus according to claim 1, wherein the first and second signals are each an electrical signal, and each transducer configured to apply the electrical signal is an electrode.

3. The apparatus according to claim 1, wherein the first and second physiological responses are each one or more of: an increase in bladder capacity, an increase in bladder voiding efficiency, a decrease in urinary retention, a decrease in the sensation of urgency, a decrease in incontinence and/or a change in external urethral sphincter (EUS) activity towards that of a healthy individual.

4. The apparatus according to claim 1, wherein the apparatus further comprises a detector to detect one or more physiological parameters in the subject, wherein the controller is coupled to said detector, and causes the first signal to be applied when a physiological parameter is detected to be meeting or exceeding a first predefined threshold value, and causes the second signal to be applied when a physiological parameter is detected to be meeting or exceeding a second predefined threshold value.

5. The apparatus according to claim 4, wherein one or more of the detected physiological parameters is selected from nerve activity in the pudendal nerve, nerve activity in the hypogastric nerve, nerve activity in the pelvic nerve, muscle activity in the bladder detrusor muscle, muscle activity in the internal urethral sphincter, muscle activity in the external urethral sphincter, muscle activity in the external anal sphincter, and bladder pressure.

6. The apparatus according to claim 1, further comprising an input element, wherein the input element allows the subject to enter data regarding their behaviour and/or desires so as to determine the timing of when the controller causes the first and second signals to be applied.

7. The apparatus according to claim 1, wherein the apparatus is suitable for at least partial implantation into the subject, optionally full implantation into the subject.

8. A method of treating bladder dysfunction in a subject by phase-specific stimulation of neural activity in a pudendal nerve of the subject, the method comprising:
applying a first signal that stimulates neural activity in the pudendal nerve to produce a first physiological response in the subject, and
applying a second signal that stimulates neural activity in the pudendal nerve to produce a second physiological response in the subject, wherein the first physiological response and second physiological response are different, and wherein the first signal is timed to be applied during a filling phase and the second signal is timed to be applied during a voiding phase.

9. The method according to claim 8, wherein the first and second physiological responses produced in the subject as a result of the first and second signal being applied are each selected from one or more of: an increase bladder capacity, an increase in bladder voiding efficiency, a decrease in urinary retention, a decrease in the sensation of urgency, a decrease in incontinence and/or a change in external urethral sphincter (EUS) activity towards that of a healthy individual.

10. The method according to claim 8, wherein the signals are applied by a neuromodulation apparatus comprising at least one transducer configured to apply the signals.

11. The method according to claim 8, wherein the signals are applied by an apparatus comprising:
at least one transducer configured to apply a signal to said nerve; and
a controller coupled to the transducer(s) and controlling the signal to be applied by the transducer(s),
wherein the controller is configured to cause at least one transducer to apply the first signal, and the controller is configured to cause at least one transducer to apply the second signal.

12. The method according to claim 10, wherein the neuromodulation apparatus is at least partially implanted in the subject, optionally wholly implanted in the subject.

13. The method according to claim 8, wherein treatment of the condition is indicated by an improvement in a measurable physiological parameter, wherein said measurable physiological parameter is at least one of: a reduction in number of incontinence episodes, a decrease in urgency of urination, a decrease in frequency of urination, an increase bladder capacity, an increase in bladder voiding efficiency.

14. The method according to claim 8, further comprising the step of detecting one or more physiological parameters in the subject, said parameters being selected from: nerve activity in the pudendal nerve, nerve activity in the hypogastric nerve, nerve activity in the pelvic nerve, muscle activity in the bladder detrusor muscle, muscle activity in the internal urethral sphincter, muscle activity in the external urethral sphincter, muscle activity in the external anal sphincter, and bladder pressure.

15. The method according to claim 14, wherein the first signal is timed to be applied when a physiological parameter is detected to be meeting or exceeding a first predefined threshold value, and the second signal is timed to be applied when a physiological parameter is detected to be meeting or exceeding a second predefined threshold value.

16. The method according to claim 8, wherein each signal is an electrical signal and, when the signals are applied by a neuromodulation apparatus, each transducer configured to apply the signals is an electrode.

17. The method according to claim 8, wherein the method is applied unilaterally or, alternatively, bilaterally.

18. A neuromodulation system comprising a plurality of apparatuses for stimulating neural activity in a pudendal nerve of a subject, wherein each apparatus comprises:
at least one transducer configured to apply a signal to said nerve; and
a controller coupled to the transducer(s) and controlling the signal to be applied by the transducer(s),
wherein the controller is configured to cause at least one transducer to apply a first signal that stimulates neural activity in the pudendal nerve to produce a first physiological response in the subject, and the controller is configured to cause at least one transducer to apply a second signal that stimulates neural activity in the pudendal nerve to produce a second physiological response in the subject, wherein the first physiological response and second physiological response are different, and wherein the first signal is timed to be applied during a filling phase and the second signal is timed to be applied during a voiding phase.

* * * * *